(12) United States Patent
Jordan et al.

(10) Patent No.: US 6,777,421 B2
(45) Date of Patent: Aug. 17, 2004

(54) 1,3,8-TRIAZASPIRO[4.5]DECAN-4-ONE DERIVATIVES USEFUL FOR THE TREATMENT OF ORL-1 RECEPTOR MEDIATED DISORDERS

(75) Inventors: Alfonzo Jordan, North Wales, PA (US); Allen B. Reitz, Lansdale, PA (US); Kevin Pan, Shanghai (CN)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 10/117,674

(22) Filed: Apr. 5, 2002

(65) Prior Publication Data

US 2003/0109539 A1 Jun. 12, 2003

Related U.S. Application Data

(60) Provisional application No. 60/282,722, filed on Apr. 10, 2001.

(51) Int. Cl.[7] .................. A61K 31/4353; C07D 403/04

(52) U.S. Cl. ........................................ 514/278; 546/20

(58) Field of Search ............................ 546/20; 514/278

(56) References Cited

U.S. PATENT DOCUMENTS

| | | | |
|---|---|---|---|
| 3,155,699 A | 11/1964 | Powers | |
| 3,629,267 A | 12/1971 | Kaiser | |
| 4,526,896 A | 7/1985 | Scherrer et al. | |
| 6,071,925 A | 6/2000 | Adam et al. | |
| 6,172,076 B1 | 1/2001 | Embrey et al. | |
| 6,235,747 B1 * | 5/2001 | Lowe et al. | 514/278 |
| 6,262,066 B1 | 7/2001 | Tulshian et al. | |
| 6,277,991 B1 | 8/2001 | Hohlweg et al. | |

FOREIGN PATENT DOCUMENTS

| | | |
|---|---|---|
| EP | 0856514 A1 | 5/1998 |
| EP | 0997464 A1 | 3/2000 |
| JP | 169476 A | 6/2000 |
| WO | 97/36871 * | 10/1997 |
| WO | WO 01/39723 A | 8/1998 |
| WO | WO 99/59997 A1 | 11/1999 |
| WO | WO 99/65494 A1 | 12/1999 |
| WO | WO 00/06545 A1 | 2/2000 |
| WO | WO 00/15222 A1 | 3/2000 |
| WO | WO 00/31037 A1 | 6/2000 |
| WO | WO 01/07050 A1 | 2/2001 |
| WO | WO 01/36418 A | 5/2001 |

OTHER PUBLICATIONS

Selway et al, Bioorganic & Medicinal vol. 4, No 5 pp. 645–654 1996.*

International PCT Search Report PCT/US02/10736, dated Jul. 15, 2002.

Zenichi, I.; "4–Oxoimidazolidine–5–Spiro–Nitrogen–Containing Heterocyclic Compound"; Patent Abstracts of Japan, Oct. 13, 2000 & jp2000169476 (Banyu Pharmaceut Co Ltd., vol. 2000, No. 09, abstract.

Henderson G, et al; "The orphan opioid receptor and its endogenous ligand–nociceptin/orphanin FQ"; Trends in Pharmacological Sciences, Elsevier Trends Journal, pp. 293–300, Aug. 1, 1997, vol. 18, No. 8, XP004085920; ISSN: 0165–6147, Cambridge, GB.

Selway, C. N. et al; "Parallel–compound synthesis: methodology for accelerating drug discovery"; Biorg. Med. Chem., 1996, pp. 645–654, vol. 4, No. 5, XP002203777, Great Britain.

Thurkauf, A. et al; "2–Pheynl–4–(aminomethyl)imidazoles as Potential Antipsychotic Agents. Synthesis and Dopamine D2 Receptor Binding"; J. Med. Chem., 1995, pp. 2251–2255, vol. 38, No. 12, XP002203778.

Thurkauf, A. et al; "3–Aminomethylbiphenyls. A New Class of Dopamine Receptor Ligands"; Med Chem Res, 1996, pp. 69–80, vol. 6.

(List continued on next page.)

*Primary Examiner*—Rita Desai

(57) ABSTRACT

The present invention is directed to novel 1,3,8-triazaspiro [4.5]decan-4-one derivatives of the general formula

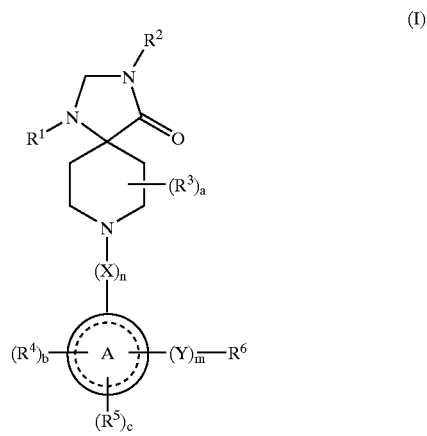

(I)

wherein all variables are as defined herein, useful in the treatment of disorders and conditions mediated by the ORL-1 G-protein coupled receptor. More particularly, the compounds of the present invention are useful in the treatment of disorders and conditions such as anxiety, depression, substance abuse, neuropathic pain, acute pain, migraine, asthma, cough and for improved cognition.

14 Claims, No Drawings

OTHER PUBLICATIONS

Thurkauf, A. et al; "1–Pheynl–3–(aminomethyl)pyrroles as Potential Antipsychotic Agents. Synthesis and Dopamine Receptor Binding"; J. Med. Chem., 1995, pp. 4950–4952, vol. 38, No. 25.

Wolfe, J. et al; "Palladium–Catalyzed Amination of Aryl Triflates"; J Org Chem, 1997, pp. 1264–1267, vol. 62, No. 5.

Wolfe, J. et al; "Rational Development of Practical Catalysts for Aromatic Carbon–Nitrogen Bond Formation"; Accounts of Chemical Research, 1998, pp. 805–818, vol. 31, No. 12.

Higgins, G. et al; "A Combined Pharmalogical and Genetic Approach to Studying the Role of Orphanin FQ on Cognition"; European Journal of Neuroscience, Jun. 24–28, 2000, p. 294.

* cited by examiner

1,3,8-TRIAZASPIRO[4.5]DECAN-4-ONE DERIVATIVES USEFUL FOR THE TREATMENT OF ORL-1 RECEPTOR MEDIATED DISORDERS

CROSS REFERENCE TO RELATED APPLICATION

This application claims priority form U.S. provisional application Serial No. 60/282,722, filed Apr. 10, 2001, the contents of which are hereby incorporated by reference.

The present invention is directed to novel 1,3,8-triazaspiro[4.5]decan-4-one derivatives useful in the treatment of disorders and conditions mediated by the ORL-1 G-protein coupled receptor. More particularly, the compounds of the present invention are useful in the treatment of disorders and conditions such as anxiety, depression, substance abuse, neuropathic pain, acute pain, migraine, asthma, cough and for improved cognition.

BACKGROUND OF THE INVENTION

The ORL-1 (orphan opioid receptor) G-protein coupled receptor, also known as the nociceptin receptor, was first reported in 1994, and was discovered based on its homology with the classic delta-, mu-, and kappa-opioid receptors. The ORL-1 G-protein coupled receptor does not bind opioid ligands with high affinity. The amino acid sequence of ORL-1 is 47% identical to the opioid receptors overall, and 64% identical in the transmembrane domains. (*Nature*, 1995, 377, 532.)

The endogenous ligand of ORL-1, known as nociceptin, a highly basic 17 amino acid peptide, was isolated from tissue extracts in 1995. It was named both nociceptin, because it increased sensitivity to pain when injected into mouse brain, and orphanin FQ (OFQ) because of the terminal phenylalanine (F) and glutamine (O) residues that flank the peptide on either side. (WO97/07212)

Nociceptin binding to ORL-1 receptors causes inhibition of cAMP synthesis, inhibition of voltage-gated calcium channels, and activation of potassium conductance. In vivo, nociceptin produces a variety of pharmacological effects that at times oppose those of the opioids, including hyperalgesia and inhibition of morphine-induced analgesia. Mutant mice lacking nociceptin receptors show better performance in learning and memory tasks. These mutant mice also have normal responses to painful stimuli.

The ORL-1 receptor is widely distributed/expressed throughout the human body, including in the brain and spinal cord. In the spinal cord, the ORL-1 receptor exists in both the dorsal and ventral horns, and precursor mRNA has been found in the superficial lamina of the dorsal horn, where primary afferent fibers of nociceptors terminate. Therefore, the ORL-1 has an important role in nociception transmission in the spinal cord. This was confirmed in recent studies wherein nociceptin, when given to mice by i.c.v. injection, induced hyperalgesia and decreased locomotor activity. (*Brit. J. Pharmacol.* 2000, 129, 1261.)

Adam, et al., in U.S. Pat. No. 6,071,925 (and in EP 0856514) disclose 1,3,8-triazaspiro[4,5]decan-4-one derivatives, agonists and/or antagonists of the OFQ receptor. More recently, Higgins, et. al., in European Forum of Neuroscience 2000, Brighton, U.K., Jun. 24–28, 2000, Poster 077.22 disclosed, 8-[(1R,3aS)-2,3,3a,4,5,6-hexahydro-1H-phenalen-1-yl]-1-phenyl-1,3,8-triazaspiro[4.5]decan-4-one useful as a cognition enhancers. Adam et al., in EP 921125-A1 disclose 1,3,8-triazaspiro[4.5]decan-4-one derivatives, agonists and/or antagonists of the OFQ receptor.

Ito, et al., in EP 0997464 disclose 1,3,8-triazaspiro[4.5]decan-4-one compounds as ORL-1 receptor agonists.

Watson, et al., in WO 99/59997 disclose 1,3,8-triazaspiro[4.5]decan-4-ones with high affinity for opioid receptor subtypes, useful for the treatment of migraine, type II diabetes, sepsis, inflammation, incontinence and/or vasomotor disturbance.

JP2000169476, assigned to Banyu Pharmaceutical Co., Ltd, disclose 4-oxoimidazolidine-5-spiro-nitrogen containing heterocyclic compounds which inhibit binding of nociceptin to the ORL1 receptor.

We now describe novel small molecule modulators of the ORL-1 receptor, useful for the treatment of disorders and conditions mediated by the ORL-1 receptor, such as anxiety, depression, substance abuse, neuropathic pain, acute pain, migraine, asthma, cough and for improved cognition.

SUMMARY OF THE INVENTION

The present invention is directed to compounds of the general formula

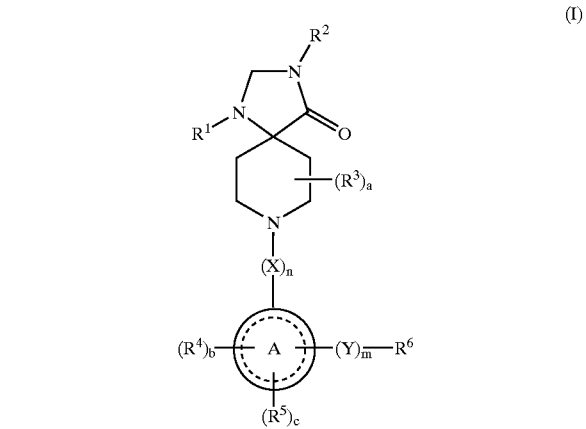

wherein $R^1$ is selected from the group consisting of hydrogen, $C_{1-6}$alkyl, aryl and aralkyl;

wherein the aryl or aralkyl group is optionally substituted with one to four substituents independently selected from halogen, $C_{1-6}$alkyl, halogenated $C_{1-6}$alkyl, $C_{1-6}$alkoxy, nitro, amino, ($C_{1-6}$alkyl)amino, di($C_{1-6}$alkyl)amino, $C_{1-6}$alkylsulfonyl, amido, ($C_{1-6}$alkyl)amido, di($C_{1-6}$alkyl)amido, sulfonyl, aminosulfonyl, ($C_{1-6}$alkyl)aminosulfonyl, di($C_{1-6}$alkyl)aminosulfonyl or $C_{3-8}$cycloalkyl;

$R^2$ is selected from the group consisting of hydrogen, $C_{1-6}$alkyl, $C_{2-6}$alkenyl, $C_{2-6}$alkynyl, hydroxyamino $C_{1-6}$alkyl, aminocarbonyl$C_{1-6}$alkyl, $C_{1-6}$alkoxycarbonyl$C_{1-6}$alkyl, aryl, $C_{3-8}$cycloalkyl, partially unsaturated carbocyclyl, heteroaryl, heterocycloalkyl, $C_{1-6}$aralkyl, carbocyclyl$C_{1-6}$alkyl, heteroaryl$C_{1-6}$alkyl, heterocycloalkyl$C_{1-6}$alkyl and phthalimidoyl$C_{1-6}$alkyl;

wherein the alkyl group is optionally substituted with one to two substituents independently selected from hydroxy, carboxy, cyano, amino, $C_{1-6}$alkylamino, di($C_{1-6}$alkyl)amino, hydroxy$C_{1-6}$alkylamino, amino $C_{1-6}$alkylamino, $C_{1-6}$alkylamino$C_{1-6}$alkylamino or di($C_{1-6}$alkyl)amino$C_{1-6}$alkylamino, wherein the aryl, cycloalkyl, carbocyclyl, heteroaryl or heterocycloalkyl group is optionally substituted with one to four substituents independently selected from halogen, $C_{1-6}$alkyl, halogenated $C_{1-6}$alkyl, $C_{1-6}$alkoxy, nitro, amino, $(C_{1-6}$alkyl)amino, di$(C_{1-6}$alkyl)amino, $C_{1-6}$alkylsulfonyl, amido, $(C_{1-6}$alkyl)amido, di$(C_{1-6}$alkyl)amido, sulfonyl, aminosulfonyl, $(C_{1-6}$alkyl)aminosulfonyl, di$(C_{1-6}$alkyl)aminosulfonyl or $C_{1-4}$alkoxycarbonyl;

a is an integer from 0 to 2;

$R^3$ is selected from the group consisting of $C_{1-4}$alkyl and hydroxy $C_{1-4}$alkyl;

n is an integer from 0 to 1;

X is selected from the group consisting of $C_{1-6}$alkyl, $C_{2-6}$alkenyl, $C_{2-4}$alkyl-O and $C_{2-4}$alkyl-S;

wherein the alkyl group is optionally substituted with one to two substituents independently selected from fluoro, $C_{1-6}$alkyl, fluorinated $C_{1-6}$alkyl, $C_{1-6}$alkoxy, nitro, amino, $(C_{1-6}$alkyl)amino, di$(C_{1-6}$alkyl)amino, $C_{1-6}$alkylsulfonyl, amido, $(C_{1-6}$alkyl)amido, di$(C_{1-6}$alkyl)amido, sulfonyl, aminosulfonyl, $(C_{1-6}$alkyl)aminosulfonyl or di$(C_{1-6}$alkyl)aminosulfonyl;

and wherein X is $C_{2-4}$alkyl-O or $C_{2-4}$alkyl-S, the X group is incorporated into the molecule such that the $C_{2-4}$alkyl is bound directly to the piperidine portion of the molecule;

is selected from the group consisting of phenyl, a five membered heteroaryl and a six membered heteroaryl;

b is an integer from 0 to 1;

$R^4$ is selected from the group consisting of aryl, $C_{3-8}$cycloalkyl, partially unsaturated carbocyclyl, heteroaryl and heterocycloalkyl;

c is an integer from 0 to 3;

$R^5$ is selected from the group consisting of halogen, $C_{1-6}$alkyl, halogenated $C_{1-6}$alkyl, $C_{1-6}$alkoxy, nitro, amino, $(C_{1-6}$alkyl)amino, di$(C_{1-6}$alkyl)amino, $C_{1-6}$alkylsulfonyl, amido, $(C_{1-6}$alkyl)amido, di$(C_{1-6}$alkyl)amido, sulfonyl, aminosulfonyl, $(C_{1-6}$alkyl)aminosulfonyl or di$(C_{1-6}$alkyl)aminosulfonyl;

m is an integer from 0 to 1;

Y is selected from the group consisting of $C_{1-4}$alkyl, $C_{2-4}$alkenyl, O, S, NH, N($C_{1-4}$alkyl), $C_{1-6}$alkyl-O, $C_{1-6}$alkyl-S, O—$C_{1-6}$alkyl and S—$C_{1-6}$alkyl-S;

$R^6$ is selected from the group consisting of aryl, partially unsaturated carbocyclyl, $C_{3-8}$cycloalkyl, heteroaryl, heterocycloalkyl and benzoyloxyphenyl;

wherein the aryl, partially unsaturated carbocyclyl, $C_{3-8}$cycloalkyl, heteroaryl or heterocycloalkyl group is optionally substituted with one to four substituents independently selected from halogen, hydroxy, $C_{1-6}$alkyl, halogenated $C_{1-6}$alkyl, $C_{1-6}$alkoxy, nitro, amino, $(C_{1-6}$alkyl)amino, di$(C_{1-6}$alkyl)amino, $C_{1-6}$alkylsulfonyl, amido, $(C_{1-6}$alkyl)amido, di$(C_{1-6}$alkyl)amido, sulfonyl, aminosulfonyl, $(C_{1-6}$alkyl)aminosulfonyl, di$(C_{1-6}$alkyl)aminosulfonyl or triphenylmethyl;

provided that when a is 0, $R^1$ is phenyl, $R^2$ is hydrogen, n is 1, X is $CH_2$,

is phenyl, b is 0, c is 0 and m is 0, then $R^6$ is selected from the group consisting of partially unsaturated carbocyclyl, $C_{3-8}$cycloalkyl, heteroaryl, heterocycloalkyl, benzoyloxyphenyl and substituted aryl; (i.e. not aryl, not phenyl)

wherein the aryl, partially unsaturated carbocyclyl, $C_{3-8}$cycloalkyl, heteroaryl or heterocycloalkyl group is optionally substituted with one to four substituents independently selected from halogen, $C_{1-6}$alkyl, halogenated $C_{1-6}$alkyl, $C_{1-6}$alkoxy, nitro, amino, $(C_{1-6}$alkyl)amino, di$(C_{1-6}$alkyl)amino, $C_{1-6}$alkylsulfonyl, amido, $(C_{1-6}$alkyl)amido, di$(C_{1-6}$alkyl)amido, sulfonyl, aminosulfonyl, $(C_{1-6}$alkyl)aminosulfonyl, di$(C_{1-6}$alkyl)aminosulfonyl or triphenylmethyl;

provided further that when a is 0, $R^1$ is phenyl, $R^2$ is hydrogen, n is 1, X is $C_{1-3}$alkyl,

is phenyl, b is 0, c is 0 and m is 0, then $R^6$ is not substituted thiazolyl; wherein the substituent on the thiazolyl is selected from amino, $C_{1-4}$alkylamino, di$(C_{1-4}$alkyl)amino or nitro;

provided further that when a is 0, $R^1$ is phenyl, $R^2$ is hydrogen, n is 1, X is $CH_2$, b is 0, c is 0 and m is 0, and $R^6$ is phenyl, then

is not imidazolyl or pyrrolyl;

and pharmaceutically acceptable salts thereof.

Illustrative of the invention is a pharmaceutical composition comprising a pharmaceutically acceptable carrier and any of the compounds described above. An illustration of the invention is a pharmaceutical composition made by mixing any of the compounds described above and a pharmaceutically acceptable carrier. Illustrating the invention is a process for making a pharmaceutical composition comprising mixing any of the compounds described above and a pharmaceutically acceptable carrier.

Exemplifying the invention are methods of treating disorders and conditions mediated by the ORL-1 receptor in a subject in need thereof comprising administering to the subject a therapeutically effective amount of any of the compounds or pharmaceutical compositions described above.

An example of the invention is a method of treating a condition selected from the group consisting of anxiety, depression, substance abuse, neuropathic pain, acute pain, migraine, asthma, cough and for improved cognition, in a subject in need thereof comprising administering to the subject a therapeutically effective amount of any of the compounds or pharmaceutical compositions described above.

Another example of the invention is the use of any of the compounds described herein in the preparation of a medicament for treating: (a) anxiety, (b) depression, (c) substance abuse (d) neuropathic pain, (e) acute pain, (f) migraine, (g) asthma and for (h) improved cognition, in a subject in need thereof.

DETAILED DESCRIPTION OF THE INVENTION

The present invention provides 1,3,8-triazaspiro[4.5]decan-4-one derivatives useful for the treatment of disorders and conditions mediated by the ORL-1 receptor. More particularly, the compounds of the present invention are of the formula (I)

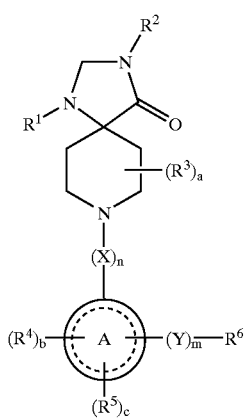

wherein $R_1$, $R^2$, a, $R^3$, n, X,

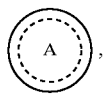

b, $R^4$, c, $R^5$, m, Y and $R^6$ are as herein defined, and pharmaceutically acceptable salts thereof.

In an embodiment of the invention $R^1$ is selected from the group consisting of hydrogen, $C_{1-6}$alkyl, aryl, substituted aryl and aralkyl. Preferably $R^1$ is selected from the group consisting of $C_{1-4}$alkyl, aryl, substituted aryl and aralkyl, wherein the aryl group is substituted with a substituent selected from halogen, $C_{1-4}$alkyl, $C_{1-4}$alkoxy, trifluoromethyl and $C_{5-6}$cycloalkyl. More preferably, $R^1$ is selected from the group consisting of n-propyl, phenyl, 4-fluorophenyl, 3-trifluoromethylphenyl, 4-methylphenyl, 4-methoxyphenyl, 4-cyclopentylphenyl, 3-bromophenyl, 3-chlorophenyl, 4-chloro-3-methylphenyl and 4-fluoro-3,5-dimethylphenyl.

In an embodiment of the invention $R^2$ is selected from the group consisting of hydrogen, $C_{1-6}$alkyl, substituted $C_{1-6}$alkyl, $C_{2-6}$alkenyl, $C_{2-6}$alkynyl, hydroxyamino$C_{1-6}$alkyl, amino$C_{1-6}$alkyl, $(C_{1-6}$alkyl)amino$C_{1-6}$alkyl, di$(C_{1-6}$alkyl)amino$C_{1-6}$alkyl, aminocarbonyl$C_{1-6}$alkyl, carboxy$C_{1-6}$alkyl, $C_{1-6}$alkoxycarbonyl$C_{1-6}$alkyl, aryl, substituted aryl, $C_{3-8}$cycloalkyl, substituted $C_{3-8}$cycloalkyl, partially unsaturated carbocyclyl, substituted partially unsaturated carbocyclyl, heteroaryl, substituted heteroaryl, heterocycloalkyl, substituted heterocycloalkyl, $C_{1-6}$aralkyl, carbocyclyl$C_{1-6}$alkyl, heteroaryl$C_{1-6}$alkyl, heterocycloalkyl$C_{1-6}$alkyl and phthalimidoyl$C_{1-6}$alkyl. Preferably, $R^2$ is selected from the group consisting of hydrogen, $C_{1-4}$alkyl, hydroxy$C_{1-4}$alkyl, cyano$C_{1-4}$alkyl, amino$C_{1-4}$alkyl, $C_{1-4}$alkylamino$C_{1-4}$alkyl, di$(C_{1-4}$alkyl) amino$C_{1-4}$alkyl, aminocarbonyl$C_{1-4}$alkyl, carboxy$C_{1-4}$alkyl, $C_{1-4}$alkoxycarbonyl$C_{1-4}$alkyl, phthalimidoyl$C_{1-4}$alkyl and substituted oxazolyl$C_{1-4}$alkyl. More preferably, $R^2$ is selected from the group consisting of hydrogen, methyl, cyanomethyl, 2-hydroxyethyl, aminoethyl, dimethylaminoethyl, diethylaminoethyl, aminocarbonylmethyl, carboxymethyl, methoxycarbonylmethyl, phthalimidoylethyl and 4-methoxycarbonyl-5-oxazolylmethyl.

In an embodiment of the invention a is an integer from 0 to 2, preferably a is an integer from 0 to 1. Preferably, $R^3$ is selected from the group consisting of $C_{1-4}$alkyl and hydroxy$C_{1-4}$alkyl.

In a preferred embodiment of the invention n is 1.

In an embodiment of the invention, X is selected from the group consisting of $C_{1-6}$alkyl, substituted $C_{1-6}$alkyl, $C_{2-6}$alkenyl, $C_{2-4}$alkyl-O and $C_{2-4}$alkyl-S. Preferably, X is selected from the group consisting of $C_{1-6}$alkyl, substituted $C_{1-6}$alkyl, $C_{2-4}$alkyl-O and $C_{2-4}$alkyl-S. More preferably, X is selected from the group consisting of $C_{1-4}$alkyl and $C_{2-4}$alkyl-O, most preferably, $C_1$alkyl ($CH_2$), $C_2$alkyl ($CH_2CH_2$), $C_3$alkyl ($CH_2CH_2CH_2$), $C_4$alkyl ($CH_2CH_2CH_2CH_2$) and $C_2$alkyl-O ($CH_2CH_2$—O).

Wherein X is $C_{2-4}$alkyl-O or $C_{2-4}$alkyl-S group, X is incorporated into the molecule such that the $C_{2-4}$alkyl is bound directly to the piperidine portion of the molecule In an embodiment of the invention

is selected from the group consisting of phenyl, a five membered heteroaryl and a six membered heteroaryl, preferably

is selected from phenyl, a five membered heteroaryl other than imidazolyl or pyrrolyl and a six membered heteroaryl. More preferably,

is selected from the group consisting of phenyl, furyl, thienyl, pyridyl and pyrazolyl.

In an embodiment of the invention b is 0. In another embodiment of the invention c is an integer from 0 to 2. In yet another embodiment of the invention c is an integer from 0 to 1. In yet another embodiment of the invention c is 0.

In an embodiment of the invention $R^5$ is selected from the group consisting of halogen, fluorinated$C_{1-4}$alkyl and $C_{1-4}$alkyl. Preferably $R^5$ is selected from the group consisting of halogen, methyl and trifluoromethyl. More preferably $R^5$ is selected from the group consisting of fluoro, chloro, methyl and trifluoromethyl. More preferably still $R^5$ is selected from the group consisting of fluoro, methyl and trifluoromethyl, more preferably still $R^5$ is selected from fluoro or methyl.

In an embodiment of the invention, Y is selected from the group consisting of $C_{1-4}$alkyl, $C_{2-4}$alkenyl, O, S, NH, N($C_{1-4}$ alkyl), $C_{1-6}$alkyl-O, $C_{1-6}$alkyl-S, O—$C_{1-6}$alkyl and S—$C_{1-6}$ alkyl-S. Preferably, Y is selected from the group consisting of O, $C_{1-4}$alkyl-O, $C_{2-4}$alkenyl and $C_{1-4}$alkyl. More preferably, Y is selected from the group consisting of O, $CH_2$—O, CH=CH and $CH_2$.

In an embodiment of the invention, $R^6$ is selected from the group consisting of aryl, substituted aryl, partially unsaturated carbocyclyl, substituted partially unsaturated carbocyclyl, $C_{3-8}$cycloalkyl, substituted $C_{3-8}$cycloalkyl, heteroaryl, substituted heteroaryl, heterocycloalkyl and substituted heterocycloalkyl. Preferably, $R^6$ is selected from the group consisting of aryl, partially unsaturated carbocyclyl, heteroaryl, heterocycloalkyl, hydroxyphenyloxymethyl and benzoyloxyphenyl, wherein the aryl, heteroaryl or heterocycloalkyl is optionally substituted with one to two substituents independently selected from halogen, acetyl, $C_{1-4}$alkyl, $C_{1-4}$alkoxy, trifluoromethyl, amino, $C_{1-4}$alkylamino, di($C_{1-4}$ alkyl)amino, cyano, nitro, oxo, t-butoxycarbonyl and triphenylmethyl. More preferably, $R^6$ is selected from the group consisting of 3-methylphenyl, 4-methylphenyl, 3,5-dichlorophenyl, 4-methoxyphenyl, 3-trifluoromethylphenyl, 3-pyridyl, 2-furyl, 3-furyl, 2-thienyl, 3-thienyl, 2-pyrrolyl, 1-naphthyl, 2-naphthyl, 2-(1-Boc-pyrrolyl), 1-(1,2,3,4-tetrahydronaphthyl), phenyl, 4-dimethylaminophenyl, 4-pyridyl, 3-quinolinyl, 2-benzothienyl, 2-benzofuryl, 5-indolyl, 2-thiazolyl, 5-chloro-2-thienyl, 5-acetyl-2-thienyl, 5-methyl-2-thienyl, 5-cyano-2-thienyl, 4-methyl-2-thienyl, 3,5-dimethyl-4-isoxazolyl, 3-pyridyl, 4-chlorophenyl, 1-(5,6,7,8-tetrahydronaphthyl), 4-hydroxyphenyloxymethyl, 1-piperidinyl, 1-(1,2,3,4-tetrahydroquinolinyl), 2-(1,2,3,4-tetrahydroisoquinolinyl), 1-pyrrolidinyl, 1-phthalimidoyl, 1-imidazolyl, 3-imidazolyl, 1-triphenylmethyl-3-imidazolyl, 1-(2-piperidinoyl), 3-chlorophenyl, 4-nitrophenyl, 4-bromophenyl, 4-chlorophenyl and benzoyloxyphenyl. Most preferably, $R^6$ is selected from the group consisting of 3-methylphenyl, 4-methylphenyl, 3,5-dichlorophenyl, 4-methoxyphenyl, 3-trifluoromethylphenyl, 3-pyridyl, 2-furyl, 3-furyl, 2-thienyl, 3-thienyl, 2-pyrrolyl, 1-naphthyl, 2-naphthyl, 2-(1-Boc-pyrrolyl), 1-(1,2,3,4-tetrahydronaphthyl), phenyl, 4-dimethylaminophenyl, 4-pyridyl, 3-quinolinyl, 2-benzothienyl, 2-benzofuryl, 5-indolyl, 5-chloro-2-thienyl, 5-acetyl-2-thienyl, 5-methyl-2-thienyl, 5-cyano-2-thienyl, 4-methyl-2-thienyl, 3,5-dimethyl-4-isoxazolyl, 3-pyridyl, 4-chlorophenyl, 1-(5,6,7,8-tetrahydronaphthyl), 4-hydroxyphenyloxymethyl, 1-piperidinyl, 1-(1,2,3,4-tetrahydroquinolinyl), 2-(1,2,3,4-tetrahydroisoquinolinyl), 1-pyrrolidinyl, 1-phthalimidoyl, 1-imidazolyl, 3-imidazolyl, -triphenylmethyl-3-imidazolyl, 1-(2-piperidinoyl), 3-chlorophenyl, 4-nitrophenyl, 4-bromophenyl 4-chlorophenyl and benzoyloxyphenyl.

In an embodiment of the invention $R^6$ is not thiazolyl or substituted thiazolyl. In another embodiment of the invention,

is not imidazolyl or pyrrolyl.

As used herein, "halogen" shall mean chlorine, bromine, fluorine and iodine.

As used herein, the term "alkyl", whether used alone or as part of a substituent group, include straight and branched chains. For example, alkyl radicals include methyl, ethyl, propyl, isopropyl, butyl, isobutyl, sec-butyl, t-butyl, pentyl and the like. Unless otherwise noted, "lower" when used with alkyl means a carbon chain composition of 1–4 carbon atoms.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like.

As used herein, unless otherwise noted, "aryl" shall refer to unsubstituted carbocylic aromatic groups such as phenyl, naphthyl, and the like.

As used herein, unless otherwise noted, "aralkyl" shall mean any lower alkyl group substituted with an aryl group such as phenyl, naphthyl and the like. For example, benzyl (phenylmethyl), phenylethyl, phenylpropyl, naphthylmethyl, and the like.

As used herein, unless otherwise noted, the term "cycloalkyl" shall mean any stable 3–8 membered monocyclic, carbon based, saturated ring system, for example cyclopropyl, cyclobutyl, cyclopentyl, cyclohexyl, cycloheptyl and cyclooctyl.

As used herein, unless otherwise noted, the term "carbocyclyl" shall mean any four to fourteen membered monocyclic or bicyclic, carbon based ring structure. Similarly, unless otherwise noted, the term "partially unsaturated carbocyclyl" shall mean any four to fourteen membered monocyclic or bicyclic, carbon based ring structure containing at least one unsaturated bond. Suitable examples include 1,2, 3,4-tetrahydronaphthyl, cyclohexen-1-yl, and the like.

As used herein, unless otherwise noted, "heteroaryl" shall denote any five or six membered monocyclic aromatic ring structure containing at least one heteroatom selected from the group consisting of O, N and S, optionally containing one to three additional heteroatoms independently selected from the group consisting of O, N and S; or a nine or ten membered bicyclic aromatic ring structure containing at least one heteroatom selected from the group consisting of O, N and S, optionally containing one to four additional heteroatoms independently selected from the group consisting of O, N and S. The heteroaryl group may be attached at any heteroatom or carbon atom of the ring such that the result is a stable structure.

Examples of suitable heteroaryl groups include, but are not limited to, pyrrolyl, furyl, thienyl, oxazolyl, imidazolyl, pyrazolyl, isoxazolyl, thiazolyl, isothiazolyl, triazolyl, thiadiazolyl, pyridyl, pyridazinyl, pyrimidinyl, pyrazinyl, pyranyl, furazanyl, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, and the like. Preferred heteroaryl groups include thienyl, pyridyl, furyl, pyrrolyl, thiazolyl, oxazolyl, isoxazolyl, indolyl, isoindolyl, quinolinyl, benzofuryl and benzothienyl.

As used herein, the term "heterocycloalkyl" shall denote any five to seven membered monocyclic, saturated or partially unsaturated ring structure containing at least one heteroatom selected from the group consisting of O, N and S, optionally containing one to three additional heteroatoms independently selected from the group consisting of O, N and S; or a nine to ten membered saturated, partially unsaturated or partially aromatic bicyclic ring system containing at least one heteroatom selected from the group consisting of O, N and S, optionally containing one to four additional heteroatoms independently selected from the group consisting of O, N and S. The heterocycloalkyl group may be attached at any heteroatom or carbon atom of the ring such that the result is a stable structure.

Examples of suitable heterocycloalkyl groups include, but are not limited to, pyrrolinyl, pyrrolidinyl, dioxalanyl, imidazolinyl, imidazolidinyl, pyrazolinyl, pyrazolidinyl, piperidinyl, dioxanyl, morpholinyl, dithianyl, thiomorpholinyl, piperazinyl, trithianyl, indolinyl, chromenyl, 3,4-methylenedioxyphenyl, 2,3-dihydrobenzofury, 1,2,3,4-tetrahydroisoquinolinyl, 1,2,3,4-tetrahydroquinolinyl, and the like. Preferred heterocycloalkyl groups include pyrrolidinyl, piperidinyl, imidazolyl, 1,2,3,4-tetrahydroisoquinolinyl and 1,2,3,4-tetrahydroquinolinyl.

As used herein, the notation "*" shall denote the presence of a stereogenic center.

When a particular group is "substituted" (e.g., alkyl, aryl, carbocyclyl, heterocycloalkyl, heteroaryl), that group may have one or more substituents, preferably from one to five substituents, more preferably from one to three substituents, most preferably from one to two substituents, independently selected from the list of substituents.

Suitable alkyl substituents include hydroxy, carboxy, cyano, amino, $C_{1-6}$alkylamino, di($C_{1-6}$alkyl)amino, hydroxy$C_{1-6}$alkylamino, amino$C_{1-6}$alkylamino, $C_{1-6}$alkylamino$C_{1-6}$alkylamino and di($C_{1-6}$alkyl)amino$C_{1-6}$alkylamino.

Suitable cycloalkyl, aryl, carbocyclyl, heteroaryl and heterocycloalkyl substituents include halogen, hydroxy, $C_{1-6}$alkyl, halogenated $C_{1-6}$alkyl, $C_{1-6}$alkoxy, nitro, amino, ($C_{1-6}$alkyl)amino, di($C_{1-6}$alkyl)amino, $C_{1-6}$alkylsulfonyl, amido, ($C_{1-6}$alkyl)amido, di($C_{1-6}$alkyl)amido, sulfonyl, aminosulfonyl, ($C_{1-6}$alkyl)aminosulfonyl, di($C_{1-6}$alkyl)aminosulfonyl and $C_{3-8}$cycloalkyl. Preferably, the cycloalkyl, aryl, carbocyclyl, heteroaryl and heterocycloalkyl substituents include halogen, $C_{1-6}$alkyl, halogenated $C_{1-6}$alkyl, $C_{1-6}$alkoxy, nitro, amino, ($C_{1-6}$alkyl)amino, di($C_{1-6}$alkyl)amino, $C_{1-6}$alkylsulfonyl, amido, ($C_{1-6}$alkyl)amido, di($C_{1-6}$alkyl)amido, sulfonyl, aminosulfonyl, ($C_{1-6}$alkyl)aminosulfonyl and di($C_{1-6}$alkyl)aminosulfonyl.

With reference to substituents, the term "independently" means that when more than one of such substituents is possible, such substituents may be the same or different from each other.

Under standard nomenclature used throughout this disclosure, the terminal portion of the designated side chain is described first, followed by the adjacent functionality toward the point of attachment. Thus, for example, a "phenyl$C_1$-$C_6$alkylcarbonylamino$C_1$-$C_6$alkyl" substituent refers to a group of the formula

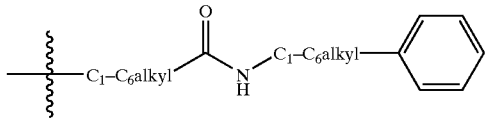

Abbreviations used in the specification, particularly the Schemes and Examples, are as follows:

| | | |
|---|---|---|
| AcOH | = | Acetic Acid |
| aq. | = | Aqueous |
| DCE | = | Dichloroethane |
| DCM | = | Dichloromethane |
| DEAD | = | Diethylazodicarboxylate |
| DIAD | = | Diisopropylazodicarboxylate |
| DIPEA or DIEA | = | Diisopropylethylamine |
| DMF | = | N,N-Dimethylformamide |

-continued

| | | |
|---|---|---|
| DME | = | 1,2-dimethoxyethane |
| DMSO | = | Dimethylsulfoxide |
| EGTA | = | Ethylene glycol-bis[β-aminoethylester]-N,N,N',N'-tetraacetic acid |
| Et$_2$O | = | Diethyl ether |
| EtOAc | = | Ethyl acetate |
| EtOH | = | Ethanol |
| HPLC | = | High Pressure Liquid Chromatography |
| KO-t-Bu | = | Potassium t-butoxide |
| MeOH | = | Methanol |
| Ms | = | mesyl group (—SO$_2$—CH$_3$) |
| Na(OAc)$_3$BH | = | Sodium triacetoxyborohydride |
| NaO-t-Bu | = | Sodium t-butoxide |
| NMP | = | N-methyl-2-pyrrolidinone |
| PEI | = | Polyethylenimine |
| Ph | = | Phenyl |
| Pd$_2$(OAc)$_2$ | = | Palladium(II)acetate |
| Pd$_2$(dba)$_3$ | = | Tris(dibenzylidene acetone)dipalladium(0) |
| Pd(PPh$_3$)$_4$ | = | tetrakis(triphenylphosphine)palladium(0) |
| PdCl$_2$(PPh$_3$)$_2$ | = | di(chloro)di(triphenylphosphine)palladium(0) |
| t-BOC or Boc | = | Tert-Butoxycarbonyl |
| t-Bu | = | Tert-butyl |
| TEA or Et$_3$N | = | Triethylamine |
| TFA | = | Trifluoroacetic Acid |
| THF | = | Tetrahydrofuran |
| TLC | = | Thin Layer Chromatography |
| TMOF | = | Trimethylorthoformate |
| Tris HCl or Tris-Cl | = | Tris[hydroxymethyl]aminomethyl hydrochloride |

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following:

acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Compounds of formula (I) wherein n is an integer from 0 to 1, m is an integer from 0 to 1, Y is selected from $C_{2-4}$alkenyl and $R^6$ is aryl or heteroaryl, may be prepared according to the process outlined in Scheme 1.

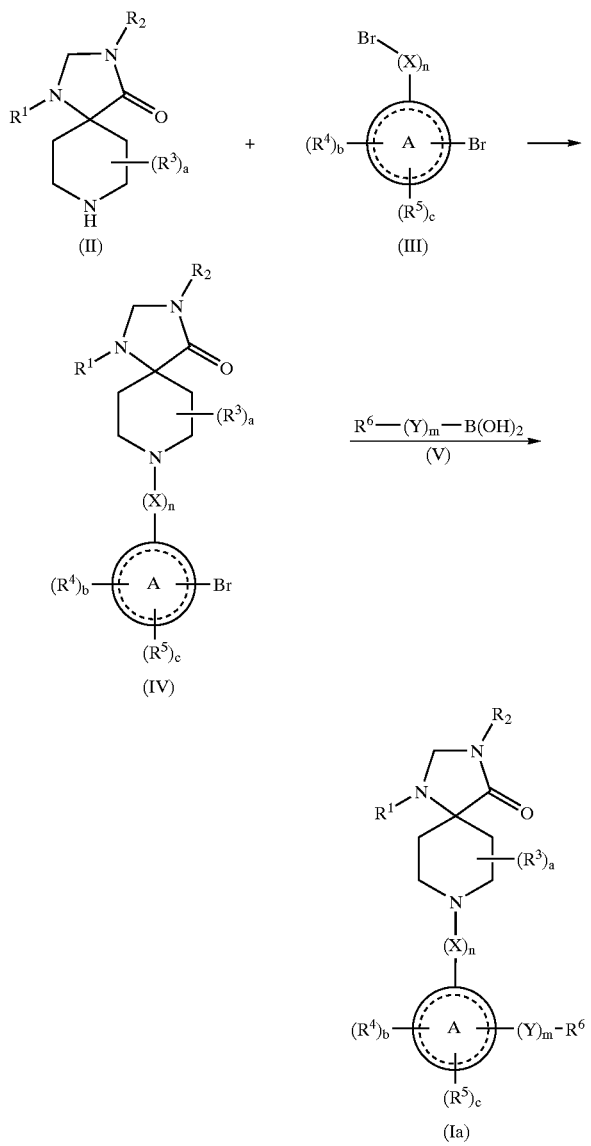

More particularly, a compound of formula (II), a known compound or compound prepared by known methods, is reacted with a suitably substituted compound of formula (III), a known compound or compound prepared by known methods, in the presence of a base such as DIPEA, TEA, pyridine, $Na_2CO_3$, $K_2CO_3$, and the like, wherein the base is present in an amount of at least one equivalent, in an organic solvent such as acetonitrile, DMF, DMSO, NMP, and the like, preferably at an elevated temperature, to yield the corresponding compound of formula (IV).

When the base is an inorganic base such as $Na_2CO_3$, $K_2CO_3$, and the like, the compound of formula (II) is reacted with the compound of formula (III) in an aprotic solvent such as DMF, DMSO, NMP, and the like.

The compound of formula (IV) is reacted with a suitably substituted boronic acid, a compound of formula (V), a known compound or compound prepared by known methods, in the presence of a catalyst such as $Pd(PPh_3)_4$, $PdCl_2(PPh_3)_2$, and the like, in the presence of a base such as $Na_2CO_3$, $NaHCO_3$, $K_3PO_4$, and the like, in a non-protic organic solvent or mixture thereof such as toluene, toluene/ethanol, DME, DMF, and the like, to yield the corresponding compound of formula (Ia).

Compounds of formula (I) wherein n is an integer from 0 to 1, m is 0 and $R^6$ is aryl or heteroaryl, may alternatively be prepared according to the process outlined in Scheme 2.

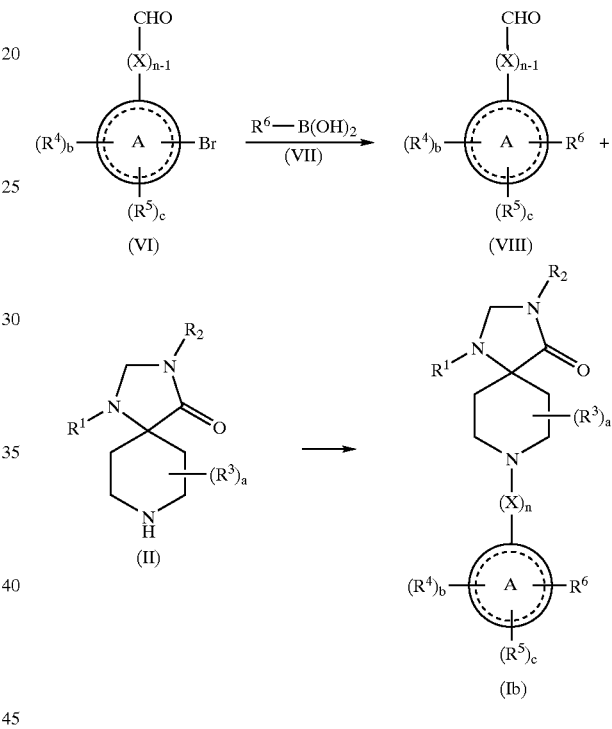

Specifically, a suitably substituted bromoaldehyde, a compound of formula (VI), a known compound or compound prepared by known methods, is reacted with a suitably substituted boronic acid, a compound of formula (VII), a known compound or compound prepared by known methods, in the presence of a catalyst such as $Pd(PPh_3)_4$, $PdCl_2(PPh_3)_2$, and the like, in the presence of a base such as $Na_2CO_3$, $NaHCO_3$, $K_3PO_4$, and the like, in a non-protic organic solvent or mixture thereof such as toluene, toluene/ethanol, DME, DMF, benzene, and the like, to yield the corresponding compound of formula (VIII).

The compound of formula (VIII) is reacted with a suitably substituted compound of formula (II), a known compound or compound prepared by known methods, in the presence of a reducing agent such as sodium triacetoxyborohydride ($Na(OAc)_3BH$), sodium cyanoborohydride ($NaCNBH_3$), and the like, optionally in the presence of an acid such as acetic acid (AcOH), and the like, in an organic solvent such as DCE, THF, acetonitrile, and the like, to yield the corresponding compound of formula (Ib).

The compound of formula (VIII) may alternatively be prepared according to the process outlined in Scheme 3.

Scheme 3

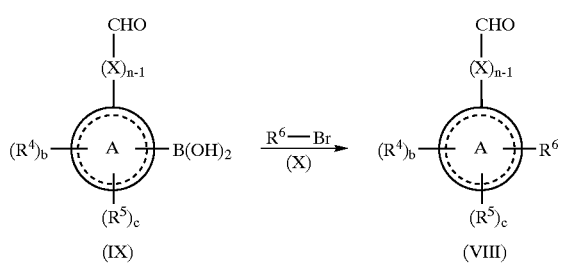

Accordingly, a suitably substituted compound of formula (IX), a known compound or compound prepared by known methods, is reacted with a suitably substituted compound of formula (X), a known compound or compound prepared by known methods, in the presence of a catalyst such as $Pd(PPh_3)_4$, $PdCl_2(PPh_3)_2$, and the like, in the presence of a base such as aqueous $NaHCO_3$, $Na_2CO_3$, $K_3PO_4$, and the like, in an organic solvent such as DME, DMF, toluene, benzene, and the like, to yield the corresponding compound of formula (VIII).

Compounds of formula (I) wherein n is 1, X is $CH_2$, m is 1, Y is O and $R^6$ is aryl or heteroaryl, may be prepared according to the process in Scheme 4.

Scheme 4

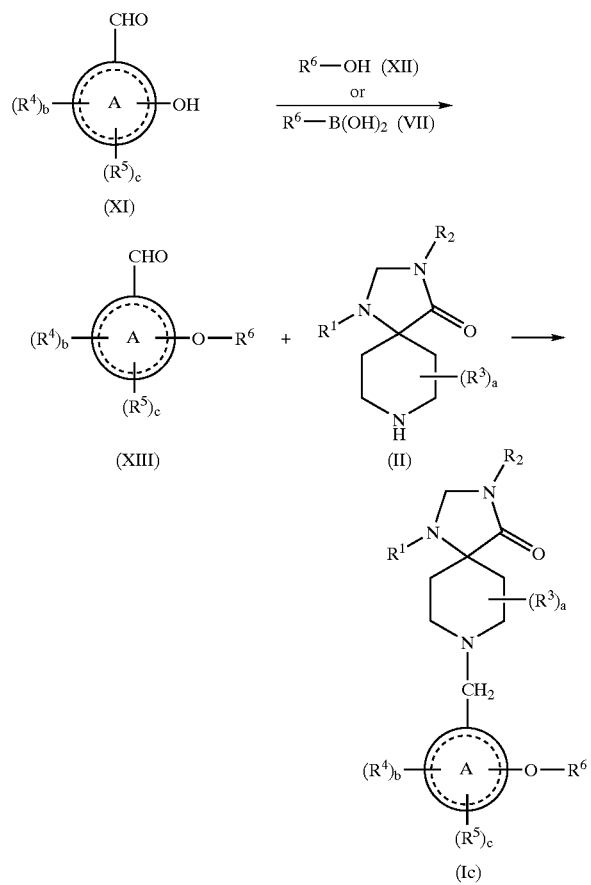

More particularly, for compounds of formula (I) wherein Y is O and $R^6$ is bound to the O through a tetrahedral carbon (i.e. a carbon atom that is not part of a unsaturated bond), a compound of formula (XI), a known compound or compound prepared by known methods, is reacted with a suitably substituted alcohol, a compound of formula (XII), a known compound or compound prepared by known methods, in the presence of an activating agent such as tributylphosphine, triphenylphosphine, diphenyl-2-pyridylphosphine, and the like, in an anhydrous organic solvent such as benzene, THF, DCM, and the like, (via a Mitsunobu reaction) in the presence of a dehydrating agent such as 1,1'-(azodicarbonyl)dipiperidine, diethylazodicarboxylate, diisopropylazodicarboxylate, and the like, to yield the corresponding compound of formula (XIII).

For compounds of formula (I) wherein Y is O and $R^6$ is bound to the O through a carbon atom that is part of a double bond (i.e. a carbon atom which is part of an aryl, heteroaryl or other unsaturated group), the compound of formula (XI) is reacted with a suitably substituted boronic acid, a compound of formula (VII), a known compound or compound prepared by known methods, in the presence of a catalyst such as copper (II) acetate, and the like, in the presence of an base such as TEA, pyridine, and the like, in the presence of molecular sieves, preferably 4 Angstrom molecular sieves, in an organic solvent such as DCM, DCE, and the like, at ambient temperature, to yield the corresponding compound of formula (XIII).

Alternatively, the compound of formula (XIII) may be prepared by reacting a compound of formula (XI) wherein the hydroxy (OH) group is replaced with a fluoro, bromo or triflate with a compound of formula (XII), as defined above, in the presence of a base such as $K_2CO_3$, sodium carbonate, sodium bicarbonate, and the like, in a dipolar aprotic solvent such as $(CH_3)_2NCOCH_3$, DMF, DMSO, and the like.

The compound of formula (XIII) is reacted with a suitably substituted compound of formula (II), a known compound or compound prepared by known methods, in the presence of a reducing agent such as sodium triacetoxyborohydride, sodium cyanoborohydride, and the like, in an organic solvent such as DCE, THF, acetonitrile, and the like, to yield the corresponding compound of formula (Ic).

One skilled in the art will recognize that compounds of formula (I) wherein m is 1 and Y is S may similarly be prepared according to the process outlined above with appropriate selection and substitution of suitably substituted starting materials.

One skilled in the art will recognize that compounds of formula (I) wherein m is 1 and Y is NH or $N(C_{1-4}alkyl)$ may similarly be prepared according to the process outlined in Scheme 1 with suitable selection and substitution of suitably substituted starting materials (i.e. amination of the arylbromide compound of formula (IV) by reacting with a suitably substituted amine of the formula $R^6-NH_2$, in the presence of palladium (0) catalysts (e.g. Buckwald reaction) as described in Accts. Chem. Res. 1998, 31, 805.).

Compounds of formula (I) wherein n is an integer from 0 to 1, m is an integer from 0 to 1, Y is selected from $C_{2-4}alkenyl$ and $R^6$ is aryl or heteroaryl, may alternatively be prepared according to the process outlined in Scheme 5.

Scheme 5

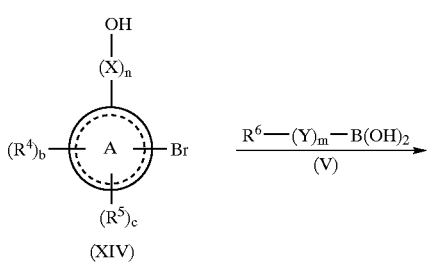

Scheme 6

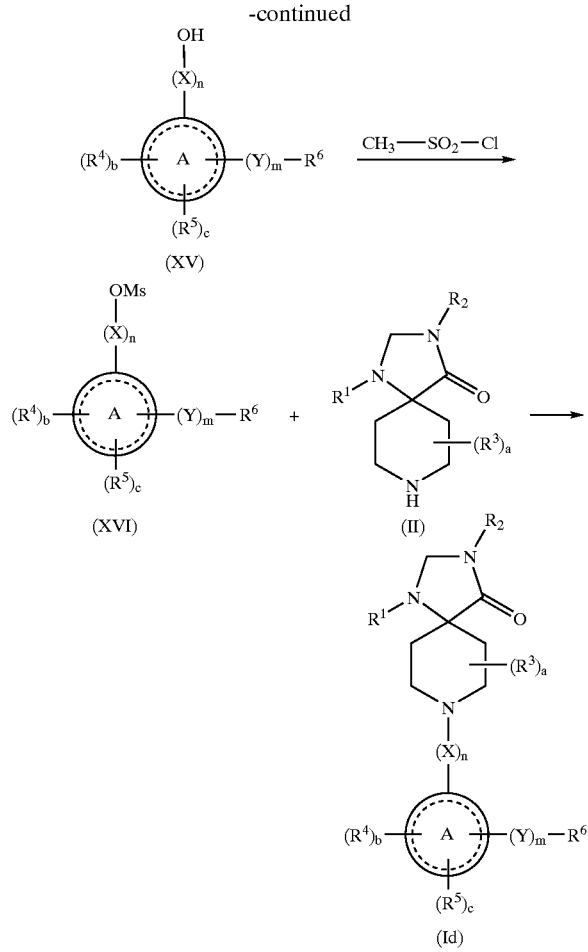

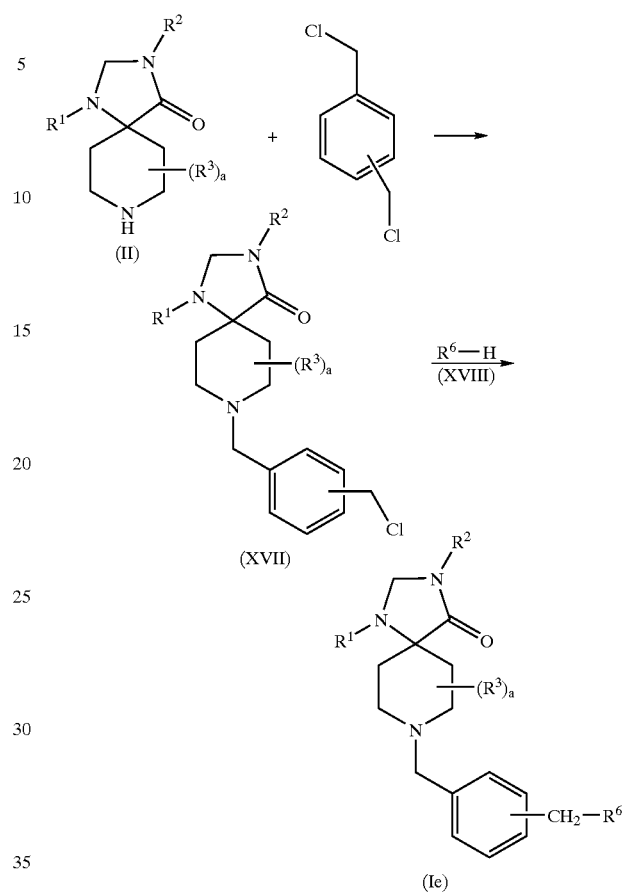

Accordingly, a suitably substituted compound of formula (XIV), a known compound or compound prepared by known methods, is reacted with a suitably substituted boronic acid, a compound of formula (V), a known compound or compound prepared by known methods, in the presence of a catalyst such as Pd(PPh$_3$)$_4$, PdCl$_2$(PPh$_3$)$_2$, and the like, in the presence of a base such as aqueous NaHCO$_3$, Na$_2$CO$_3$, K$_3$PO$_4$, and the like, in an organic solvent such as DME, benzene, and the like, to yield the corresponding compound of formula (XV).

The compound of formula (XV) is reacted with methanesulfonyl chloride, in the presence of an organic base such as TEA, DIPEA, N-methylmorpholine, and the like, in an aprotic organic solvent such as DCM, THF, acetonitrile, CHCl$_3$, and the like, to yield the corresponding compound of formula (XVI).

The compound of formula (XVI) is reacted with a suitably substituted compound of formula (II), a known compound or compound prepared by known methods, in the presence of a base such as TEA, DIPEA, pyridine, and the like, in an aprotic organic solvent such as DCE, THF, acetonitrile, NMP, and the like, to yield the corresponding compound of formula (Id).

Compounds of formula (I) wherein n is 1, X is CH$_2$,

is phenyl, m is 1, Y is —CH$_2$— and the —(Y)$_m$—R$^6$ group is bound at the 3 or 4 position (not the 2 position), may be prepared according to the process outlined in Scheme 6.

More specifically, a suitably substituted compound of formula (II), a known compound or compound prepared by known methods, is reacted with 1,4- or 1,3-bis-(chloromethyl)benzene, a known compound, in the presence of an organic base such as DIPEA, TEA, N-methylmorpholine, and the like, in an organic solvent such as NMP, DMF, acetonitrile, and the like, to yield the corresponding compound of formula (XVII), wherein the chloromethyl is bound at the 4- or 3-position, respectively.

The compound of formula (XVII) is reacted with a suitably substituted compound of formula (XVIII), a known compound or compound prepared by known methods, in the presence of a base such as TEA, DIPEA, K$_2$CO$_3$, Na$_2$CO$_3$, and the like, in an organic solvent such as NMP, DMF, THF, and the like, to yield the corresponding compound of formula (Ie), wherein the —(Y)$_m$—R$^6$ group is bound at the 4 or 3 position, respectively, Alternatively, the compound of formula (II) may be reacted with 1,3- or 2,6-di(chloromethyl)pyridyl, to yield the corresponding compound wherein the

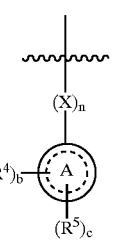

portion of the molecule is a suitably substituted pyridylmethyl rather than a suitably substituted benzyl.

Alternatively, compounds of formula (I) (X)$_n$ is CH$_2$,

is phenyl, m is 1, Y is —CH$_2$— and the —(Y)$_m$—R$^6$ group is bound at the 3 or 4 position (not the 2 position), may be prepared according to the process outlined in Scheme 7.

Scheme 7

Step 1:

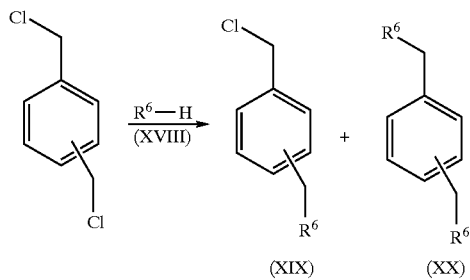

Step 2:

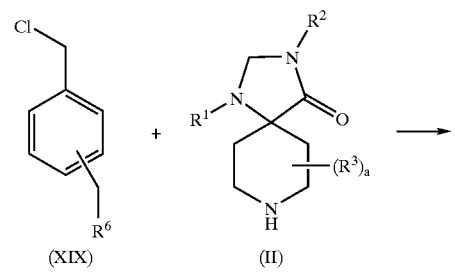

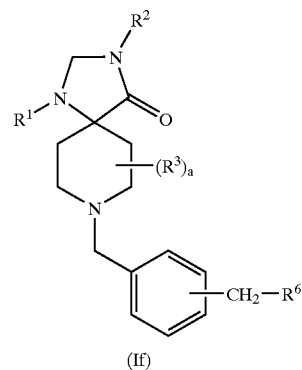

(If)

Accordingly, 1,2-, 1,3 or 1,4-substituted bischloromethyl benzene, a known compound is reacted with a suitably substituted compound of formula (XVIII), a known compound or compound prepared by known methods, in an organic solvent such as THF, DMSO, DMF, and the like, in the presence of a base such as NaH, Na$_2$CO$_3$, K$_2$CO$_3$, N-butyl lithium, and the like, to yield a mixture of the mono- and di-substituted benzene compounds of formula (XIX) and (XX).

The mono-substituted compound of formula (XIX) is preferably isolated and then reacted with a suitably substituted compound of formula (II), a known compound or compound prepared by known methods, in the presence of an organic base such as DIPEA, TEA, pyridine, N-methylmorpholine, and the like, in an organic solvent such as NMP, THF, DMF, and the like, to yield the corresponding compound of formula (If).

Compounds of formula (I) wherein n is 0 may alternatively be prepared by adapting the process described in *J. Org. Chem.* 1997, 62, 1264, and references cited therein. More particularly, the compounds of formula (I) wherein n is 0 may be prepared according to the process outlined in Scheme 8.

Scheme 8

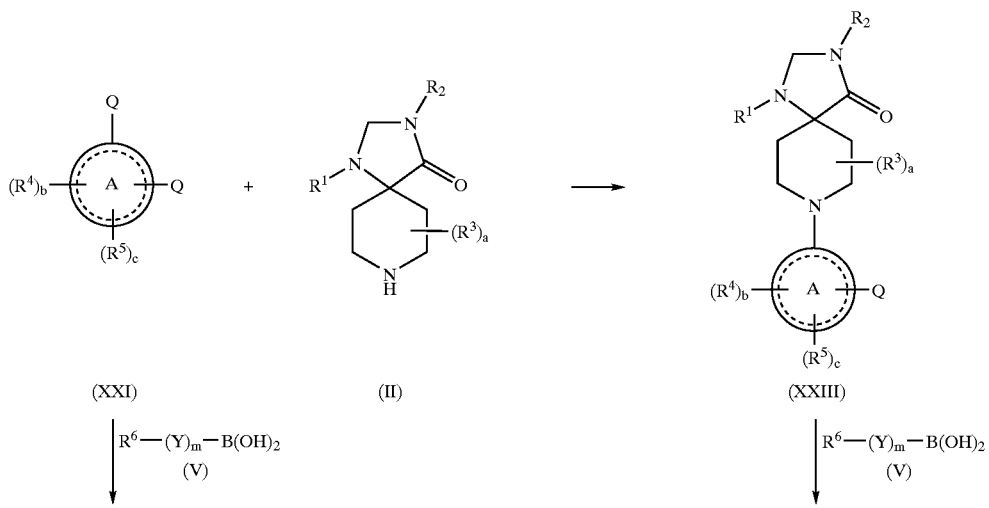

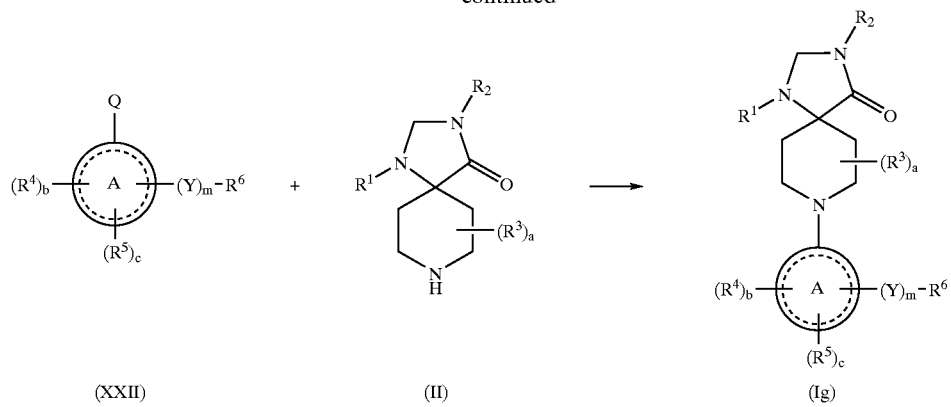

(XXII)  (II)  (Ig)

Accordingly, a suitably substituted compound of formula (XXI), wherein each Q is independently selected from —Br, —Cl or —OSO$_2$CF$_3$, a known compound or compound prepared by known methods is reacted with a suitably substituted boronic acid, a compound of formula (V), a known compound or compound prepared by known methods, in the presence of a catalyst such as Pd(PPh$_3$)$_4$, PdCl$_2$(PPh$_3$)$_2$, and the like, in an organic solvent such as DME, DMF, toluene, and the like, to yield the corresponding compound of formula (XXII).

The compound of formula (XXII) is reacted with a suitably substituted compound of formula (II), a known compound or compound prepared by known methods, in the presence of a catalyst such as Pd$_2$(dba)$_3$, Pd$_2$(OAc)$_2$, and the like, in the presence of a case such as KO-t-Bu, NaO-t-Bu, K$_3$, PO$_4$, and the like, in an organic solvent such as THF, DME, toluene, and the like, to yield the corresponding compound of formula (Ig).

Alternatively, a suitably substituted compound of formula (XXI), wherein each Q is independently selected from, —Br, —Cl or —OSO$_2$CF$_3$, a known compound or compound prepared by known methods, is reacted with a suitably substituted compound of formula (II), a known compound or compound prepared by known methods, in the presence of a catalysts such Pd$_2$(dba)$_3$, Pd$_2$(OAc)$_2$, and the like, in the presence of a case such as KO-t-Bu, NaO-t-Bu, K$_3$, PO$_4$, and the like, in an organic solvent such as THF, DME, toluene, and the like, to yield the corresponding compound of formula (XXIII)

The compound of formula (XXIII) is reacted with a suitably substituted boronic acid, a compound of formula (V), a known compound or compound prepared by known methods, in the presence of a catalyst such as Pd(PPh$_3$)$_4$, PdCl$_2$(PPh$_3$)$_2$, and the like, in the presence of a base such as Na$_2$CO$_3$, NaHCO$_3$, and the like, in an organic solvent such as DME, DMF, toluene, and the like, to yield the corresponding compound of formula (Ig).

Compounds of formula (I) wherein R$^1$ and R$^2$ are varied, may be prepared from suitably substituted starting materials according to the processes disclosed in U.S. Pat. No. 3,155,699 (Issued Nov. 3, 1964) and/or in PCT Application WO 99/59997.

Compounds of formula (I) wherein R$^2$ is selected from carboxy substituted C$_{1-6}$alkyl, aminoC$_{1-6}$alkyl, aminocarbonylC$_{1-6}$alkyl or C$_{1-6}$alkylcarbonylC$_{1-6}$alkyl, wherein the amino portion of the R$^2$ group may be optionally substituted with one or two C$_{1-6}$alkyl groups, may be prepared according to the process outlined in Scheme 9.

Scheme 9

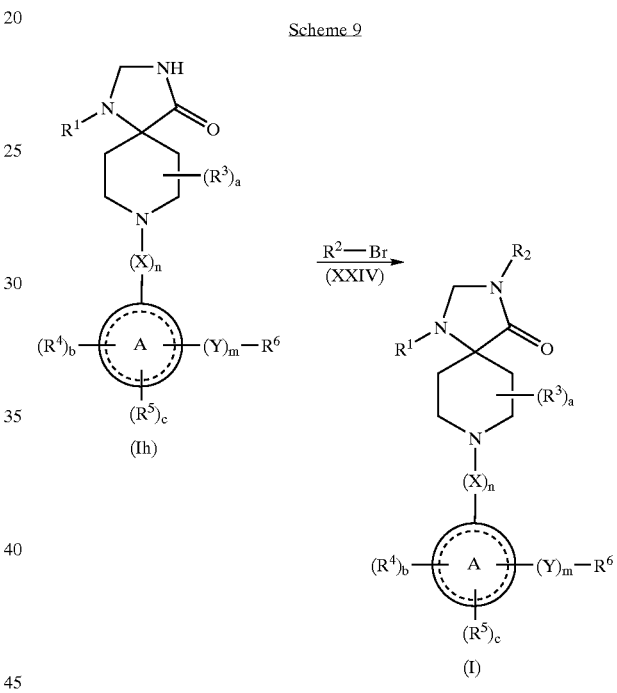

Accordingly, a suitably substituted compound of formula (Ih), (a compound of formula (I) wherein R$^2$ is hydrogen), a known compound or compound prepared by known methods, is reacted with a suitably substituted compound of formula (XXIV), a known compound or compound prepared by known methods, in the presence of a strong base such as NaH, KH, sodium trimethylsilylamide, and the like, in an organic solvent such as DMF, NMP, THF, and the like, to yield the corresponding compound of formula (I).

Alternatively, the compound of formula (Ih) is reacted with a compound of formula (XXIV), wherein the hydroxy, carboxy or amino portion of the R$^2$ group is protected, followed by de-protection by known methods, to yield the corresponding compound of formula (I).

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Following the procedures described herein, selected compounds of the present invention were prepared as listed in Table 1–10.

TABLE 1

| Cmpd # | m | Y | $R^6$ | MS MH+ |
|---|---|---|---|---|
| 1 | 0 | — | phenyl | 398.2 |
| 2 | 0 | — | 3-thienyl | 404.1 |
| 3 | 0 | — | 4-methylphenyl | 412.2 |

TABLE 1-continued

| Cmpd # | m | Y | $R^6$ | MS MH+ |
|---|---|---|---|---|
| 4 | 0 | — | 3,5-dichlorophenyl | 467.2 |
| 5 | 0 | — | 4-methoxyphenyl | 428.2 |
| 6 | 0 | — | 3-pyridyl | 399.2 |
| 7 | 0 | — | 3-trifluoromethylphenyl | 466.2 |
| 8 | 0 | — | 2-furyl | 388.2 |
| 9 | 0 | — | 2-thienyl | 404.1 |
| 10 | 0 | — | 3-furyl | 388.2 |
| 11 | 0 | — | 2-pyrrolyl | 387.2 |
| 12 | 0 | — | 1-naphthyl | 448.2 |
| 13 | 0 | — | 2-(1-Boc-pyrrolyl) | 487.3 |
| 14 | 1 | —O— | 1-(1,2,3,4-tetrahydronaphthyl) | 468.3 |
| 15 | 0 | — | 2-naphthyl | 448.2 |
| 16 | 1 | —CH$_2$—O— | phenyl | 428.4 |
| 17 | 0 | — | 4-dimethylaminophenyl | 441.3 |
| 18 | 0 | — | 4-pyridyl | 399.1 |
| 19 | 0 | — | 3-quinolinyl | 449.2 |
| 20 | 0 | — | 2-benzothienyl | 454.1 |
| 21 | 0 | — | 2-benzofuryl | 438.1 |
| 22 | 0 | — | 5-indolyl | 437.1 |
| 23 | 1 | trans —CH=CH— | phenyl | 424.2 |
| 24 | 0 | — | 2-thiazolyl | 405.1 |
| 25 | 0 | — | 5-chloro-2-thienyl | 438.0 |
| 26 | 0 | — | 5-acetyl-2-thienyl | 446.1 |
| 27 | 0 | — | 5-methyl-2-thienyl | 418.1 |
| 28 | 0 | — | 5-cyano-2-thienyl | 429.0 |
| 29 | 0 | — | 4-methyl-2-thienyl | 418.1 |
| 30 | 0 | — | 3,5-dimethyl-4-isoxazolyl | 417.1 |
| 57 | 1 | O | phenyl | 414.1 |
| 58 | 0 | — | 3-imidazolyl | 388.1 |
| 59 | 0 | — | 1-triphenylmethyl-3-imidazolyl | 630.3 |

TABLE 2

| Cmpd# | $R^1$ | $R^2$ | $(R^3)_a$ | MW MH+ |
|---|---|---|---|---|
| 31 | phenyl | dimethylaminoethyl | a = 0 | 475.0 |
| 32 | 4-fluorophenyl | hydrogen | a = 0 | 422.0 |

TABLE 2-continued

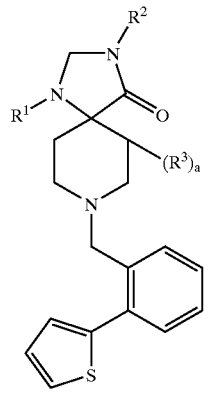

| Cmpd# | R¹ | R² | (R³)ₐ | MW MH⁺ |
|---|---|---|---|---|
| 33 | phenyl | diethylaminoethyl | a = 0 | 503.2 |
| 34 | phenyl | aminoethyl | a = 0 | 404.0 |
| 35 | phenyl | methyl | a = 0 | 418.2 |
| 36 | phenyl | aminocarbonyl methyl | a = 0 | 431.1 |
| 38 | 4-fluorophenyl | hydrogen | 5-methyl | 436.1 |
| 39 | phenyl | 2-hydroxyethyl | a = 0 | 448.1 |
| 40 | phenyl | methoxycarbonyl methyl | a = 0 | 476.1 |
| 41 | phenyl | carboxymethyl | a = 0 | 462.1 |
| 42 | 3-trifluoro methylphenyl | hydrogen | a = 0 | 472.0 |
| 43 | 4-methylphenyl | hydrogen | a = 0 | 418.1 |
| 44 | phenyl | phthalimidoylethyl | a = 0 | 577.0 |
| 45 | n-propyl | hydrogen | a = 0 | 370.1 |
| 46 | 4-cyclopentyl phenyl | hydrogen | a = 0 | 472.1 |
| 47 | 4-methoxyphenyl | hydrogen | a = 0 | 434.1 |
| 60 | 4-chloro-3-methylphenyl | hydrogen | a = 0 | 453.1 |
| 61 | 4-fluoro-3,5-dimethylphenyl | hydrogen | a = 0 | 450.1 |
| 62 | 3-bromophenyl | hydrogen | a = 0 | 483.1 |
| 63 | 3-chlorophenyl | hydrogen | a = 0 | 438.1 |
| 64 | phenylmethyl | hydrogen | a = 0 | 418.1 |
| 65 | phenyl | 4-methoxycarbonyl-5-oxazolylmethyl | a = 0 | 543.6 |

TABLE 3

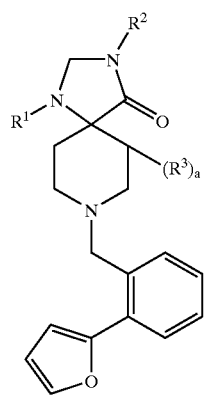

| Cmpd # | R¹ | R² | (R³)ₐ | MW MH⁺ |
|---|---|---|---|---|
| 48 | phenyl | methyl | a = 0 | 402.1 |
| 49 | phenyl | cyanomethyl | a = 0 | 413.1 |

TABLE 3-continued

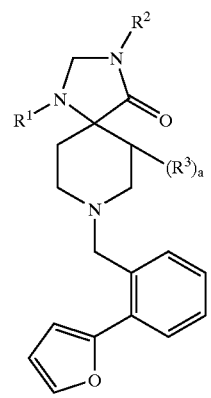

| Cmpd # | R¹ | R² | (R³)ₐ | MW MH⁺ |
|---|---|---|---|---|
| 50 | 4-fluorophenyl | hydrogen | a = 0 | 406.1 |
| 51 | 4-fluorophenyl | hydrogen | 5-methyl | 420.1 |
| 52 | 3-trifluoro methylphenyl | hydrogen | a = 0 | 456.2 |
| 53 | 4-methylphenyl | hydrogen | a = 0 | 402.2 |
| 54 | n-propyl | hydrogen | a = 0 | 354.1 |
| 55 | 4-methoxyphenyl | hydrogen | a = 0 | 418.2 |
| 56 | 4-cyclopentyl phenyl | hydrogen | a = 0 | 456.2 |
| 66 | 4-chloro-3-methylphenyl | hydrogen | a = 0 | 436.1 |
| 67 | 4-fluoro-3,5-dimethylphenyl | hydrogen | a = 0 | 434.1 |
| 68 | 3-bromophenyl | hydrogen | a = 0 | 467.1 |
| 69 | 3-chorophenyl | hydrogen | a = 0 | 422.1 |
| 70 | phenylmethyl | hydrogen | a = 0 | 402.1 |

TABLE 4

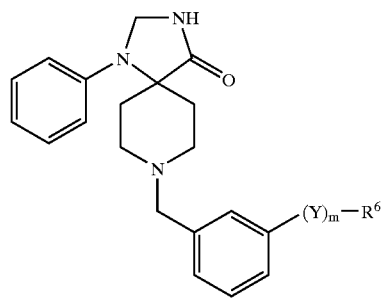

| Cmpd # | m | Y | R⁶ | MS MH⁺ |
|---|---|---|---|---|
| 101 | 1 | —CH₂—O— | phenyl | 428.3 |
| 102 | 1 | —O— | 1-(1,2,3,4-tetrahydronaphthyl) | 468.3 |
| 103 | 0 | — | 3-thienyl | 404.3 |
| 104 | 0 | — | 1-naphthyl | 448.4 |
| 105 | 0 | — | 4-methylphenyl | 412.2 |
| 106 | 0 | — | phenyl | 398.2 |

TABLE 4-continued

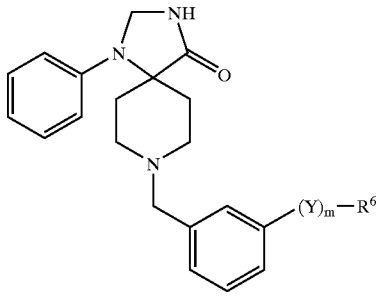

| Cmpd # | m | Y | R⁶ | MS MH⁺ |
|---|---|---|---|---|
| 107 | 0 | — | 3-trifluoromethylphenyl | 466.4 |
| 108 | 0 | — | 3,5-dichlorophenyl | 466.3 |
| 109 | 0 | — | 3-pyridyl | 399.4 |
| 110 | 0 | — | 4-methoxyphenyl | 428.4 |
| 111 | 1 | —CH₂—O— | 4-chlorophenyl | 462.4 |
| 112 | 1 | —CH₂—O— | 1-naphthyl | 478.4 |
| 113 | 1 | —CH₂—O— | 1-(5,6,7,8-tetrahydronaphthyl) | 482.3 |
| 114 | 1 | —CH₂—O— | 4-methoxyphenyl | 458.3 |
| 115 | 1 | —CH₂—O— | 4-benzoyloxyphenyl | 548.3 |
| 116 | 1 | —CH₂—O— | 4-hydroxyphenyl | 444.2 |
| 117 | 1 | —CH₂— | 1-piperidinyl | 419.3 |
| 118 | 1 | —CH₂— | 1-(1,2,3,4-tetrahydroquinolinyl) | 467.3 |
| 119 | 1 | —CH₂— | 2-(1,2,3,4-tetrahydroisoquinolinyl) | 467.3 |
| 120 | 1 | —CH₂— | 1-pyrrolidinyl | 405.3 |
| 121 | 1 | —CH₂— | 1-phthalimidoyl | 481.3 |
| 122 | 1 | —CH₂— | 1-imidazolyl | 402.3 |
| 123 | 1 | —CH₂— | 1-(2-piperidinoyl) | 433.4 |
| 124 | 1 | —CH₂—O— | 3-chlorophenyl | 462.2 |
| 125 | 1 | —CH₂—O— | 4-nitrophenyl | 473.2 |

TABLE 5

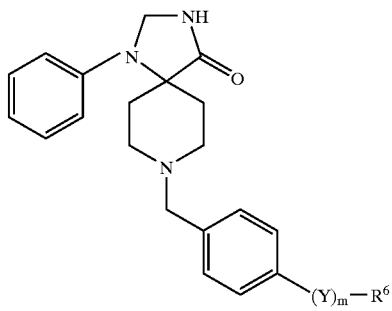

| Cmpd # | m | Y | R⁶ | MS MH⁺ |
|---|---|---|---|---|
| 201 | 1 | —CH₂—O— | phenyl | 428.31 |
| 202 | 1 | —O— | 1-(1,2,3,4-tetrahydronaphthyl) | 468.2 |
| 203 | 0 | — | phenyl | 398.3 |
| 204 | 0 | — | 3-trifluoromethylphenyl | 466.3 |
| 205 | 0 | — | 3-thienyl | 404.3 |
| 206 | 0 | — | 3-pyridyl | 399.3 |
| 207 | 0 | — | 3,5-dichlorophenyl | 466.2 |
| 208 | 0 | — | 1-naphthyl | 448.4 |
| 209 | 0 | — | 4-methoxyphenyl | 428.3 |
| 210 | 0 | — | 4-methylphenyl | 412.2 |
| 211 | 1 | —CH₂— | 1-piperidinyl | 419.3 |
| 213 | 1 | —CH₂— | 1-(2-piperidonyl) | 433.4 |
| 214 | 1 | —CH₂— | 1-pyrrolidinyl | 405.3 |
| 215 | 1 | —CH₂— | 1-imidazolyl | 402.3 |
| 216 | 1 | —CH₂— | 1-phthalimidoyl | 481.2 |
| 217 | 1 | —CH₂— | 2-(1,2,3,4-tetrahydroisoquinolinyl) | 467.3 |

TABLE 5-continued

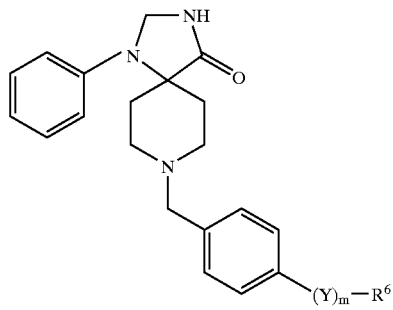

| Cmpd # | m | Y | R⁶ | MS MH⁺ |
|---|---|---|---|---|
| 218 | 1 | —CH₂— | 1-(1,2,3,4-tetrahydroquinolinyl) | 467.3 |

TABLE 6

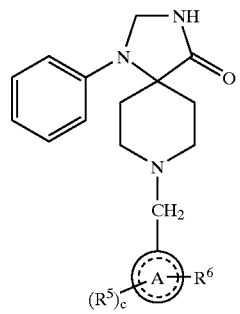

| Cmpd # | (R⁵)c / A | R⁶ | MS MH⁺ |
|---|---|---|---|
| 301 | 2-furyl | 5-(4-bromophenyl) | 467.1 |
| 302 | 2-furyl | 5-(4-chlorophenyl) | 422.2 |
| 303 | 2-chloro-4-methyl-3-pyrazoyl | phenyl | 436.0 |
| 304 | 2-methyl-3-pyrazoyl | 4-(2-thienyl) | 408.0 |
| 305 | 2-thienyl | 3(2-thienyl) | 410.0 |
| 306 | 3-pyridyl | 2-(m-tolyl) | 413.1 |

TABLE 7

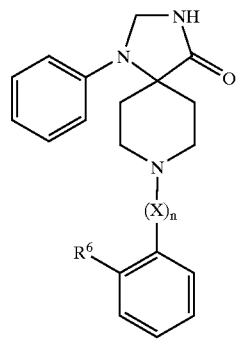

| Cmpd # | (X)n | R⁶ | MS MH⁺ |
|---|---|---|---|
| 401 | (CH₂)₂ | 2-thienyl | 418.1 |
| 402 | (CH₂)₂ | 3-thienyl | 418.0 |
| 403 | (CH₂)₃ | 2-thienyl | 432.0 |

TABLE 7-continued

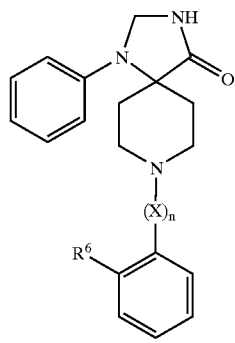

| Cmpd # | (X)ₙ | R⁶ | MS MH⁺ |
|---|---|---|---|
| 404 | (CH₂)₃ | 3-thienyl | 432.1 |
| 405 | (CH₂)₄ | 2-thienyl | 446.1 |

TABLE 8

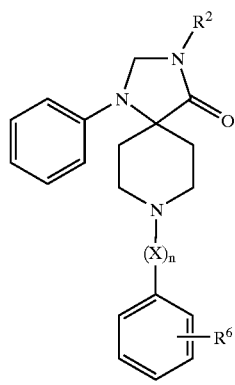

| Cmpd # | R² | (X)ₙ | R⁶ | MS MH⁺ |
|---|---|---|---|---|
| 406 | H | —CH₂CH₂—O | 2-phenyl | 428.0 |
| 407 | dimethylamino-ethyl | —CH₂CH₂— | 2-(2-thienyl) | 489.2 |
| 408 | diethylamino-ethyl | —CH₂CH₂— | 2-(2-thienyl) | 517.1 |
| 409 | Methoxycarbonyl-methyl | —CH₂CH₂— | 2-(2-thienyl) | 490.1 |
| 410 | carboxymethyl | —CH₂CH₂— | 2-(2-thienyl) | 476.1 |
| 411 | H | —CH₂CH₂— | 3-(2-thienyl) | 418.0 |
| 412 | H | —CH₂CH₂— | 4-(2-thienyl) | 418.0 |

TABLE 9

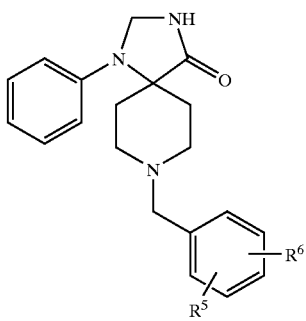

| Cmpd # | R⁵ | R⁶ | MS MH⁺ |
|---|---|---|---|
| 501 | 5-fluoro | 2-(2-thienyl) | 422.0 |
| 502 | 5-trifluoromethyl | 2-(2-thienyl) | 472.0 |

TABLE 9-continued

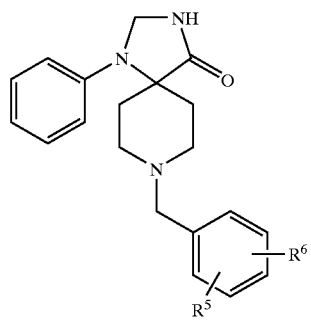

| Cmpd # | R⁵ | R⁶ | MS MH⁺ |
|---|---|---|---|
| 503 | 6-fluoro | 2-(3-thienyl) | 422.0 |
| 504 | 4-fluoro | 2-(2-thienyl) | 422.0 |
| 505 | 4-fluoro | 2-(3-thienyl) | 422.0 |

TABLE 10

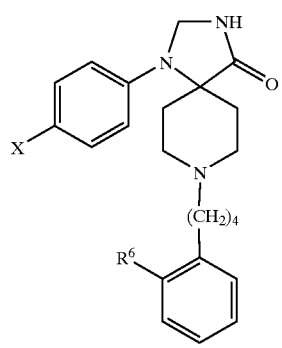

| Cmpd # | X | R⁶ | MS MH⁺ |
|---|---|---|---|
| 506 | fluoro | 2-thienyl | 464.1 |

The present invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g.

water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 5 to about 1000 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating disorders mediated by the ORL-1 receptor described in the present invention may also be carried out using a pharmaceutical composition comprising any of the compounds as defined herein and a pharmaceutically acceptable carrier. The pharmaceutical composition may contain between about 1 mg and 1000 mg, preferably about 10 to 500 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms may include suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of disorders mediated by the ORL-1 receptor is required.

The daily dosage of the products may be varied over a wide range from 5 to 1,000 mg per adult human per day. For oral administration, the compositions are preferably provided in the form of tablets containing, 1.0, 5.0, 10.0, 15.0, 25.0, 50.0, 100, 250 and 500 milligrams of the active ingredient for the symptomatic adjustment of the dosage to the patient to be treated. An effective amount of the drug is ordinarily supplied at a dosage level of from about 0.1 mg/kg to about 20 mg/kg of body weight per day. Preferably, the range is from about 0.2 mg/kg to about 10 mg/kg of body weight per day, and especially from about 0.5 mg/kg to about 10 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The following Examples are set forth to aid in the understanding of the invention, and are not intended and should not be construed to limit in any way the invention set forth in the claims which follow thereafter.

EXAMPLE 1

1-Phenyl-8-[2-[3-(trifluoromethyl)phenyl]benzyl]-1,3,8-triaza-spiro[4.5]decan-4-one (Compound #7).

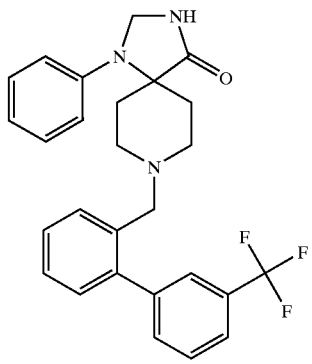

Step A

A mixture of 2-bromobenzyl bromide (0.70 mL, 4.54 mmol), 1-phenyl-1,3,8-triazaspiro[4.5]decan-4-one (1.036 g, 0.0045 mol) and diisopropylethylamine (0.86 mL, 4.95 mmol) in acetonitrile was refluxed for 1 hr. The mixture was cooled to room temperature, the precipitated product collected by filtration and dried in a vacuum oven at room temperature overnight to yield the product as a white solid.

MS (loop pos.) MH+=401.26 (25%), 403.26 (23%);

$^1$H NMR (300 MHz, DMSO-$d_6$) δ1.50–1.60 (m, 2H), 2.50–2.60 (m, 2H), 2.70–2.90 (m, 4H), 3.70 (s, 2H), 4.60 (s, 2H), 6.70–6.75 (m, 1H), 6.80–6.85 (m, 2H), 7.15–7.25 (m, 3H), 7.35–7.40 (m, 1H), 7.55–7.70 (m, 2H), 8.65 (s, 1H).

Step B

To a mixture of the product of Step A (105 mg, 0.260 mmol) and 2 M aqueous $Na_2CO_3$ (1.5 mL) in toluene (7 mL) was added a solution of 3-trifluoromethylphenyl boronic acid (108 mg, 0.572 mmol) in ethanol (2.50 mL). The resulting mixture was stirred at room temperature under nitrogen atmosphere, treated with Pd(PPh$_3$)$_4$ (18 mg, 6 mol %) and refluxed for 7 hrs. The solution was cooled to room temperature, the dark brown reaction mixture was diluted with ethyl acetate (75 mL) and washed with water (2×75 mL). The organic phase was dried over $Na_2SO_4$, filtered and concentrated to yield the crude product. The crude product was purified by chromatography on the Biotage apparatus (2% methanol in CHCl$_3$) to yield the title product as a white solid.

MS (loop pos.) MH+=466.2 (100%)

$^1$H NMR (300 MHz, CDCl$_3$) δ1.50–1.60 (m, 2H), 2.50–2.60 (m, 2H), 2.70–2.90 (m, 4H), 3.40 (s, 2H), 4.75 (s, 2H), 6.20 (s, 1H), 6.80–6.90 (m, 3H), 7.25–7.75 (m, 9H), 8.20 (s, 1H).

EXAMPLE 2

1-Phenyl-8-[2-(3-thienyl)benzyl]-1,3,8-triaza-spiro[4.5]decan-4-one (Compound #2).

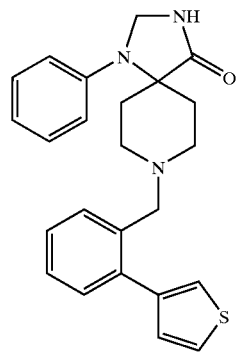

Step A

To a mixture of 2-bromobenzaldehyde (0.32 mL, 2.70 mmol) and 3 mL of 2 M aqueous sodium carbonate in 15 mL of toluene was added thiophene-3-boronic acid (384 mg, 3.00 mmol) in ethanol (3 mL). The mixture was stirred and then treated with tetrakis(triphenylphosphine)palladium (0) (93.0 mg, 3 mole %) and heated to reflux under nitrogen atmosphere for 4.5 hr. The resulting solution was cooled to room temperature, the dark brown reaction mixture was diluted with ethyl acetate (75 mL) and washed with water (2×75 mL). The organic phase was dried over $Na_2SO_4$, filtered and concentrated in vacuo to yield 2-(3-thienyl)benzaldehyde as a brown oil.

The reaction was repeated on a 50 mmol scale with 2-bromobenzaldehyde (5.8 mL), thiophene-3-boronic acid (7.03 g, 0.0555 mol) in ethanol (55 mL), Pd(PPh$_3$)$_4$ (1.7 g, 3 mol %), 2 M aqueous $Na_2CO_3$ (55 mL) in toluene (275 mL) to yield crude 2-(3-thienyl)benzaldehyde as an oil.

Both batches of the crude 2-(3-thienyl)benzaldehyde were combined and carried onto the next step without purification.

MS (loop pos.) MH+=189

$^1$H NMR (300 MHz, DMSO-$d_6$) δ7.30–7.80 (m, 7H), 10.0 (s, 1H)

Step B

To a mixture of 1-phenyl-1,3,8-triazaspiro[4.5]decan-4-one (416 mg, 1.80 mmol) and crude 2-(3-thienyl)benzaldehyde (340 mg) and acetic acid (0.1 mL, 1.80 mmol) in $CH_2Cl_2$ (14 mL) was added sodium triacetoxyborohydride (0.763 g, 3.60 mmol). The resulting mixture was stirred at room temperature for 20 hrs. The reaction mixture was quenched with 1 N aqueous NaOH and extracted with $CH_2Cl_2$ (2×). The combined extracts were washed with 1 N aqueous NaOH, dried over $K_2CO_3$, filtered, and concentrated in vacuo to yield the crude product as an oil.

The reaction was repeated on a 6.6 mmol scale with spiropiperidine (1.53 g), crude 2-(3-thienyl)benzaldehyde (1.24 g), AcOH (0.38 mL) and Na(OAc)$_3$BH (2.80 g, 0.0132 mol) in $CH_2Cl_2$ (50 mL) reacted to yield crude product as an oil.

The total combined, crude product from both experiments described above was purified by flash chromatography on silica gel (2% MeOH in $CH_2Cl_2$) to yield the title compound as a free base. The free base (2.15 g) was dissolved in isopropyl alcohol and acidified with 1 N HCl in diethyl ether to yield the title product as a monohydrochloride salt.

MS (loop pos.) MH$^+$=404.1 (100%)

$^1$H NMR (300 MHz, DMSO d$_6$) δ1.50–1.60 (m, 2H), 2.75–2.90 (m, 2H), 3.20–3.45 (m, 4H), 4.40 (s, 2H), 4.55 (s, 2H), 6.75–6.80 (m, 1H), 6.95–7.00 (m, 2H), 7.15–7.25 (m, 3H), 7.40–7.45 (m, 1H), 7.50–7.55 (m, 2H), 7.65 (m, 1H), 7.70–7.75 (m, 1H), 7.90–7.95 (m, 1H), 8.9 (s, 1H), 10.40 (br s, 1H exchangeable)

Elemental Analysis For C$_{24}$H$_{25}$N$_3$OS.HCl.0.1H$_2$O:

Calculated: C, 65.25; H, 5.98; N, 9.51; Cl, 8.02; H$_2$O, 0.41.

Measured: C, 64.93; H, 5.89; N, 9.44; Cl, 8.06; H$_2$O, 0.40.

EXAMPLE 3

1-phenyl-8-[[4-[(1,2,3,4-tetrahydro-1-naphthalenyl)oxy]phenyl]methyl]-1,3,8-triazaspiro[4.5]decan-4-one (Compound #202)

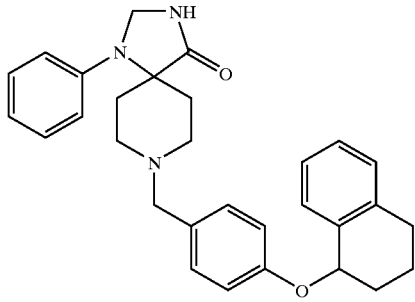

Step A

To a cold (0° C.) heterogenous mixture of 1,2,3,4-tetrahydro-1-naphthol (2.96 g, 0.020 mol) in anhydrous benzene (100 mL) was added p-hydroxybenzaldehyde (3.66 g, 0.030 mol) and tributylphosphine (6.14 g, 0.030 mol). The resultant solution was then treated with 1,1'-(azodicarbonyl)dipiperidine (7.56 g, 0.030 mol). The dark yellow reaction mixture was stirred at room temperature for 18 h, filtered and concentrated in vacuo. The crude product was purified by flash chromatography on silica gel (10% EtOAc in hexane) to yield the phenyl ether product as a white solid.

$^1$H NMR (300 MHz, CDCl$_3$) δ1.77–1.90 (m, 1H), 1.95–2.23 (m, 3H), 2.74–2.85 (m, 1H), 2.88–2.97 (m, 1H), 5.50–5.53 (m, 1H), 7.09–7.60 (m, 7H), 7.84–7.89 (m, 1H), 9.90 (s, 1H).

Step B

To a mixture of 4-(1,2,3,4-tetrahydro-1-naphthyloxy)benzaldehyde (264 mg, 1.05 mmol) and 1-phenyl-1,3,8-triazaspiro[4.5]decan-4-one (232 mg, 1.00 mmol) in 1,2-dichloroethane (15 mL) was added sodium triacetoxyborohydride (369 mg, 1.74 mmol). The resultant reaction mixture was stirred at room temperature under argon atmosphere for 20 h. The reaction mixture was quenched with 1 N aqueous NaHCO$_3$ and extracted with CHCl$_3$ (2×50 mL). The organic phase was dried over Na$_2$SO$_4$, filtered and concentrated. The crude product was purified by flash chromatography on silica gel (4% MeOH in CHCl$_3$) to yield the title product as an off-white solid.

MS (loop pos) MH$^+$=468.2 (100%)

$^1$H NMR (300 MHz, DMSO-d$_6$) δ1.50–1.60 (m, 2H), 1.70–1.80 (m, 1H), 1.85–2.05 (m, 3H), 2.50–2.65 (m, 2H), 2.70–2.85 (m, 6H), 3.45 (s, 2H), 4.55 (s, 2H), 5.45–5.45 (m, 1H), 6.75–6.80 (m, 1H), 6.85–6.90 (m, 2H), 7.00–7.05 (s, 2H), 7.15–7.35 (m, 8H), 8.60 (s, 1H).

EXAMPLE 4

1-phenyl-8-[[2-(2-thiazolyl)phenyl]methyl]-1,3,8-triazaspiro[4.5]decan-4-one (Compound #24)

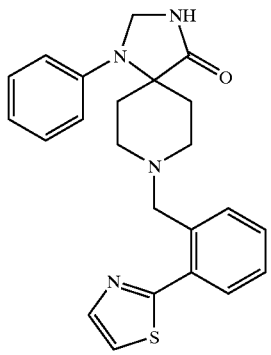

Step A

To a mixture of 2-bromothiazole (826 mg, 4.99 mmol) and tetrakis(triphenylphosphine) palladium (0) (175 mg, 0.151 mmol) in 1,2-dimethoxyethane (20 mL) was added 2-formylbenzeneboronic acid (0.9017 g, 6.01 mmol) and 1N aqueous NaHCO$_3$ (8 mL). The resultant mixture was heated at reflux for 6 hrs. The reaction mixture was diluted with water and extracted with EtOAc (2×50 mL). The organic solution was dried over Na$_2$SO$_4$, filtered and concentrated. The crude product was purified by gradient flash chromatography (10% to 25% EtOAc in hexane) to yield 2-(2-thiazolyl)benzaldehyde as a white solid.

MS (loop pos) MH$^+$=190.1

$^1$H NMR (300 MHz, CDCl3) 7.50 (m, 1H), 7.55–7.60 (m, 1H), 7.65–7.70 (m, 1H), 7.75–7.80 (m, 1H), 7.95–7.97 (m, 1H), 8.00–8.05 (m, 1H), 10.5 (s, 1H)

Step B

To a mixture of 2-(2-thiazolyl)benzaldehyde (200 mg, 1.06 mmol) and 1-phenyl-1,3,8-triazaspiro[4.5]decan-4-one (0.232 mg, 1.00 mmol) in 1,2-dichloroethane (20 mL) was added sodium triacetoxyborohydride (376 mg, 1.79 mmol). The resultant mixture was stirred at room temperature for 18 h, quenched with aqueous NaHCO$_3$ (50 mL) and extracted with CHCl$_3$ (2×50 mL). The organic solution was dried over Na$_2$SO$_4$, filtered and concentrated. The crude product was dissolved in 1:1 CHCl$_3$:CH$_3$OH (30 mL) and treated with 2 mL of 1 N HCl in Et$_2$O. The HCl salt was precipitated by addition of Et$_2$O, collected by filtration and dried in the vacuum oven at 60° C. for 18 h to yield the product as an amorphous solid.

MS (loop pos): MH$^+$=405.1 (100%)

$^1$H NMR (300 MHz, DMSO d$_6$) δ1.50–1.60 (m, 2H), 2.75–2.90 (m, 2H), 3.45–3.55 (m, 2H), 3.75–3.90 (m, 2H), 4.65 (s, 2H), 4.70 (s, 2H), 6.76–6.81 (m, 1H), 6.95–6.98 (m, 2H), 7.18–7.24 (m, 2H), 7.60–7.70 (m, 2H), 7.90–7.99 (m, 3H), 8.14–8.15 (m, 1H), 9.00 (s, 1H), 9.80 (br s, 1H exchangeable).

Compounds 58 and 59 were similarly prepared according to the procedure above with selection and substitution of a suitable reagent for the 2-bromothiazole in Step A.

EXAMPLE 5

1-phenyl-8-[2-[2-(2-thienyl)phenyl]ethyl]-1,3,8-triazaspiro[4.5]decan-4-one (Compound #401)

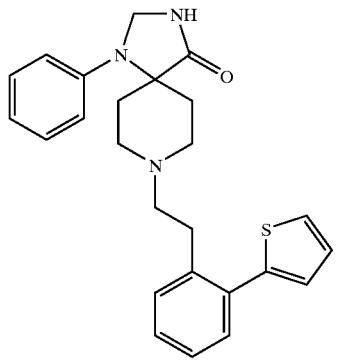

Step A

To a stirring mixture of 2-bromophenethyl alcohol (0.72 mL, 5.31 mmol) and tetrakis (triphenylphosphine) palladium (0) (620 mg, 10 mol %) in 1,2-dimethoxyethane (45 mL) was added thiophene-2-boronic acid (2.0391 g, 0.0159 mol) and 1 N aqueous $NaHCO_3$ (15 mL). The resultant reaction mixture was heated at reflux for 66 h under argon atmosphere. The dark reaction mixture was diluted with $H_2O$ (20 mL) and extracted with EtOAc (2×75 mL). The organic solution was dried over $Na_2SO_4$, filtered and concentrated. The dark residue was purified by flash chromatography on silica gel (30% EtOAc in hexane) to yield 2-(2-thienyl)phenethyl alcohol as a light yellow oil.

$^1$H NMR (300 MHz, DMSO $d_6$) δ2.87 (t, J=7.44, 7.43 Hz), 2H), 3.52–3.58 (m, 2H), 4.68 (t, J=5.17, 5.18 Hz, 1H (exchangeable)), 7.14–7.15 (m, 2H), 7.20–7.38 (m, 4H), 7.59–7.61 (m, 1H).

Step B

To a cold (0° C.) solution of 2-(2-thienyl)phenethyl alcohol (206 mg, 1.01 mmol) and triethylamine (170 μL, 1.22 mmol) in anhydrous $CH_2Cl_2$ (10 mL) was added methanesulfonyl chloride (94 μL, 1.21 mmol). Upon complete addition of the methanesulfonyl chloride, the reaction was stirred at room temperature under argon atmosphere for 1 h. The reaction mixture was then diluted with $CH_2Cl_2$ (50 mL), washed with $H_2O$ (1×25 mL), aq $NaHCO_3$ (2×25 mL), dried over $Na_2SO_4$, filtered and concentrated to yield the mesylate compound as a yellow oil, which was taken into the next step without further purification.

$^1$H NMR (300 MHz, $CDCl_3$) δ2.81 (s, 3H), 3.22 (t, J=7.12, 7.13 Hz, 2H), 4.30 (t, J=7.13, 7.12 Hz, 2H), 7.02–7.04 (m, 1H), 7.08–7.12 (m, 1H), 7.27–7.41 (m, 5H).

Step C

Crude mesylate compound prepared as in Step B (270 mg, ca 1.0 mmol), 1-phenyl-1,3,8-triazaspiro[4.5]decan-4-one (197 mg, 0.852 mmol) and diisopropylethylamine (0.20 mL, 1.15 mmol) in 1-methyl-2-pyrrolidinone (5 mL) were stirred in an preheated oil bath (60° C.) for 18 h and at 85° C. for 6 h. The reaction mixture was diluted with aq NaCl and extracted with $CHCl_3$ (2×25 mL). The organic solution with $H_2O$ (6×50 mL), dried over $Na_2SO_4$, filtered and concentrated. The crude oil was purified by flash chromatography (4% $CH_3OH$ in $CHCl_3$) to yield an oil (256 mg) which contained N-methyl-2-pyrrolidinone. The crude product was dissolved in EtOAc (25 mL), and treated with 1 mL of 1 N HCl in $Et_2O$. The HCl salt was precipitated by addition of $Et_2O$, collected by filtration and dried in the vacuum oven at 70° C. for 1 day to yield the product as an amorphous off-white solid.

MS (loop pos): $MH^+$=418.1 (100%)

$^1$H NMR (300 MHz, DMSO $d_6$) δ1.50–1.60 (m, 2H), 2.89–2.93 (m, 2H), 3.23–3.27 (m, 4H), 3.40–3.50 (m, 4H), 4.62 (s, 2H), 6.78–6.82 (m, 1H), 7.01–7.05 (m, 2H), 7.18–7.29 (m, 4H), 7.33–7.43 (m, 3H), 7.47–7.50 (m, 1H), 7.68–7.70 (m, 1H), 9.02 (s, 1H), 10.46 (br s, 1H exchangeable).

Compounds 402, 411 and 412 were similarly prepared according to the procedure described above with selection and substitution of a suitably substituted boronic acid for the thiophene-2-boronic acid in Step A.

EXAMPLE 6

8-[4-(1,2,3,4-tetrahydroquinolin-1-ylmethyl)-benzyl]-1-phenyl-1,3,8-triaza-spiro[4.5]decan-4-one (Compound # 218)

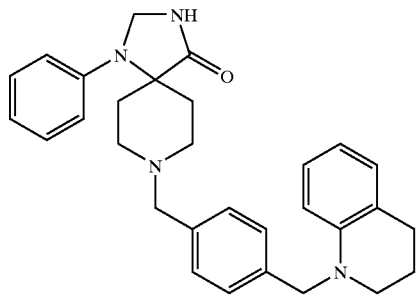

Step A

A mixture of 1-phenyl-1,3,8-triazaspiro[4.5]decan-4-one (2.3180 g, 0.010 mol), α,α-dichloro-p-xylene (5.2514 g, 0.030 mol) and diisopropylethylamine (1.484 g, 0.0114 mol) in 1-methyl-2-pyrrolidinone (45 mL) was stirred in a preheated oil bath (80° C.) for 5 h. The reaction mixture was diluted with $H_2O$ (100 mL) and extracted with EtOAc (2×200 mL). The organic phase was washed with $H_2O$ (7×100 mL), dried over $Na_2SO_4$ then filtered and concentrated. The crude beige solid was stirred in $Et_2O$ (500 mL), and filtered. The filtrate was acidified with 1N HCl in $Et_2O$ (12 mL) to yield the product as a HCl salt, which was collected by filtration as a white solid.

MS (loop pos) $MH^+$=370.1 (100%), 372.1 (33%)

$^1$H NMR (300 MHz, DMSO-$d_6$) δ1.85 (d, J=14.86 Hz, 2H), 2.91–2.96 (m, 2H), 3.35–3.50 (m, 2H), 3.64–3.68 (m, 2H), 4.36–4.38 (m, 2H), 4.60 (s, 2H), 4.80 (s, 2H), 6.77 (t, 7 Hz, 7 Hz, 1H), 7.04 (d, 8.38 Hz, 2H), 7.21 (t, 7.53, 7,53 Hz, 2H), 7.53 (d, J=7.85 Hz, 2H), 7.69 (d, J=7.55 Hz, 2H), 9.00 (s, 1H), 10.73 (s, 1H)

Step B

Benzyl chloride (0.3 mmol) was converted to its free base by partitioning HCl salt (125.5 mg) between $CH_2Cl_2$ and aqueous $NaHCO_3$. A solution of this free base in $CH_3CN$ (7 mL) was treated sequentially with 1,2,3,4-tetrahydroquinoline (0.045 mL, 0.36 mmol) and triethylamine (0.083 mL, 0.60 mmol) and then refluxed for 18 h. The reaction mixture was then cooled to room temperature, then diluted with $CH_2Cl_2$ (7 mL) and basified with 3N aqueous NaOH. The organic layer was washed with $H_2O$ (2×), dried over $Na_2SO_4$, filtered and concentrated. The crude product was purified by chromatography on the Biotage apparatus (5% MeOH in CH₂Cl₂) to yield the product as an amorphous solid.

MS (loop pos) MH⁺=467.4 (100%)

¹H NMR (300 MHz, DMSO-d₆) δ1.50–1.60 (m, 2H), 2.55–2.60 (m, 2H), 2.65–2.75 (m, 6H), 2.80–2.85 (m, 2H), 3.50–3.55 (m+s, 4H), 3.65 (s, 2H), 4.55 (s, 2H), 6.80–6.85 (m, 2H), 6.95–7.00 (m, 1H), 7.05–7.10 (m, 4H), 7.20–7.25 (m, 2H), 7.30–7.35 (m, 4H), 8.65 (s, 1H).

EXAMPLE 7

8-(2-phenoxymethyl-benzyl)-1-phenyl-1,3,8-triazaspiro[4.5]decan-4-one (Compound #16)

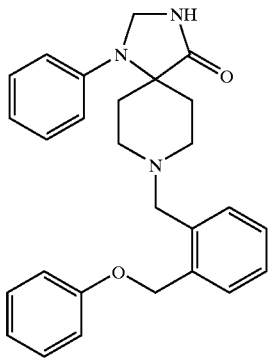

Step A

To a cold (0° C.) heterogenous mixture of unwashed 80% NaH in mineral oil (0.4641 g, 0.0155 mol) in anhydrous THF (15 mL) was added phenol (1.4148 g, 0.0155 mol) in THF (15 mL). Upon complete evolution of H₂ gas, the resultant slightly cloudy solution was treated with α,α-dichloro-o-xylene (5.2503 g, 0.0299 mol) and stirred at room temperature for 4 h. DMSO (2 mL) was then added to the reaction mixture, and then stirred for 18 h. The reaction mixture was quenched with aqueous NH₄Cl and extracted with EtOAc (100 mL). The organic solution was washed with H₂O (4×), dried over Na₂SO₄, filtered and concentrated. The crude colorless oil was gradiently chromatographed on silica gel with 100% hexane to 10% hexane in EtOAc to yield a mixture of the monoether product and the diether byproduct. The mixture was carried forward without further purification.

¹H NMR: (300 MHz, DMSO-d₆) δ4.85 (s, 2H), 5.25 (s, 2H), 6.90–7.10 (m, 3H), 7.25–7.40 (m, 5H), 7.50–7.55 (m, 1H)

Step B

A mixture of crude monoether (170 mg, 0.777 mmol), diisopropylethylamine (0.16 mL, 0.918 mmol) and 1-phenyl-1,3,8-triazaspiro[4.5]decan-4-one (179 mg, 0.777 mmol) in 2-methyl-1-pyrrolidinone (4 mL) was stirred in a preheated oil bath (80° C.) for 4 h. The reaction mixture was diluted with H₂O (50 mL), extracted with EtOAc (2×50 mL). The organic solution was dried over Na₂SO₄, filtered and concentrated. The crude product was purified by flash chromatography (4% MeOH in CHCl₃) and by tapered preparative TLC (50% EtOAc in hexane) to yield the title product as a white solid.

MS (loop pos) MH⁺=428.4 (100%)

¹H NMR (300 MHz, DMSO-d₆) δ1.50–1.60 (m, 2H), 2.45–2.55 (m, 2H), 2.65–2.75 (m, 4H), 3.60 (s, 2H), 4.55 (s, 2H), 5.40 (s, 2H), 6.65–6.75 (m, 1H), 6.80–6.85 (m, 2H), 6.85–6.90 (m, 1H), 7.05–7.10 (m, 4H), 7.25–7.35 (m, 5H), 7.50–7.55 (m, 1H), 8.65 (s, 1H).

EXAMPLE 8

8-[3-naphth-1-yloxymethyl)-benzyl]-1-phenyl-1,3,8-triaza-spiro[4.5]decan-4-one (Compound #112)

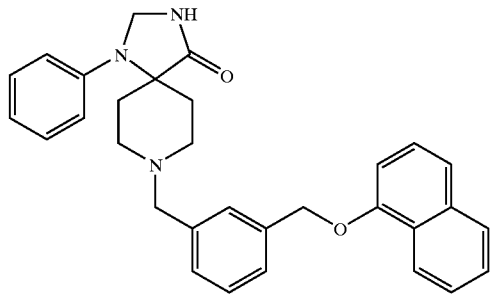

Step A

To 80% NaH in mineral oil (18.3 mg, 0.61 mmol) in DMF (20 mL) was added 1-naphthol (86.3 mg, 0.599 mmol). The resultant homogenous solution was treated with benzyl chloride (184 mg, 0.50 mmol) and stirred at room temperature under argon atmosphere for 18 h. The reaction was heated for 4 h at 60° C., treated with additional 1-naphthol (36.5 mg) and NaH (11.1 mg) and then stirred overnight at 80° C. The reaction mixture was then diluted with aqueous NH₄Cl (20 mL) and extracted with EtOAc (2×20 mL). The organic solution was dried over Na₂SO₄, filtered and concentrated. The crude product was purified by tapered prep TLC (1:1 EtOAc/hexane) to yield the product as an off-white solid.

MS (loop pos) MH⁺=478.4 (100%)

¹H NMR (300 MHz, DMSO-d₆) δ1.50–1.60 (m, 2H), 2.45–2.55 (m, 2H), 2.65–2.75 (m, 4H), 3.55 (s, 2H), 4.55 (s, 2H), 5.30 (s, 2H), 6.70–6.75 (m, 1H), 6.80–6.85 (m, 2H), 7.00–7.05 (m, 1H), 7.20–7.25 (m, 2H), 7.30–7.50 (m, 8H), 7.85–7.90 (m, 1H), 8.20–8.25 (m, 1H), 8.60 (m, 1H).

EXAMPLE 9

8-(3-phenyloxymethyl-benzyl)-1-phenyl-1,3,8-triaza-spiro[4.5]decan-4-one (Compound #101)

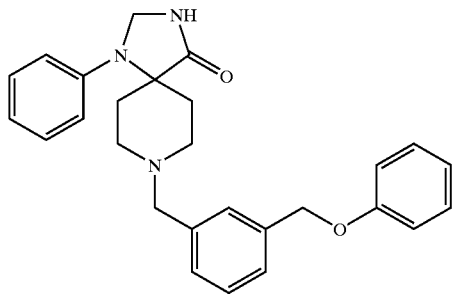

A mixture of 8-(3-chloromethyl-benzyl)-1-phenyl-1,3,8-triaza-spiro[4.5]decan-4one, prepared as in Example 8 above, (203 mg, 0.500 mmol), phenol (56.8 mg, 0.603 mmol), KI (83.1 mg, 0.500 mmol) and K₂CO₃ (174 mg, 1.26 mmol) in DMF was stirred at room temperature for 1 day. The reaction mixture was diluted with H₂O and a white solid precipitated. The solid was collected by filtration, washed with H₂O and dried under house vacuum. The crude product was initially purified by flash chromatography (5% MeOH in CHCl₃) and by tapered prep TLC (5% MeOH in CHCl₃) to yield the title product as a white amorphous solid.

MS (loop pos) MH⁺=428.3 (100%)

¹H NMR (300 MHz, DMSO-d₆) δ1.50–1.60 (m, 2H), 2.45–2.55 (m, 2H), 2.65–2.75 (m, 4H), 3.55 (s, 2H), 4.55 (s, 2H), 5.20 (s, 2H), 6.75–7.07 (m, 6H), 7.20–7.40 (m, 8H), 8.60 (m, 1H).

EXAMPLE 10

1-(4-fluorophenyl)-8-[[2-(2-thienyl)phenyl]methyl]-1,3,8-triazaspiro[4.5]decan-4-one (Compound #32)

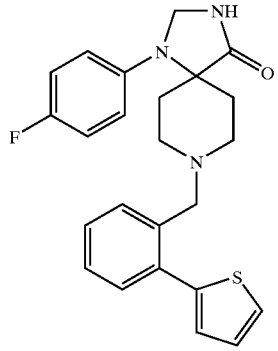

Step A

To a mixture of 2-bromobenzaldehyde (1.17 mL, 10.0 mmol) and 2.0 M aqueous sodium carbonate (75 mL) in DME (225 mL) were added thiophene-2-boronic acid (1.53 g, 12.0 mmol) and tetrakis(triphenylphosphine)palladium[0] (578 mg, 0.5 mmol). The mixture was heated to reflux under nitrogen for 16 hr. The resulting solution was cooled, and the crude product was extracted from aqueous solution with ethyl acetate. The organic layer was dried over MgSO₄, and the solvents were removed under vacuum. The crude product was purified on flash column with 25% DCM in hexane to yield 2-(2-thienyl)benzaldehyde.

Step B 2-(2-furanyl)-benzaldehyde was similarly prepared with substitution of 2-furanyl-2-boronic acid for the thiophene-2-boronic acid in the process outlined in Step A above.

Step C 2-(2-Thienyl)benzaldehyde from step A (445.0 mg, 2.36 mmol) was dissolved in anhydrous DCE (30.0 mL) and split into 30 portions. One portion was added to the solution of 1-(4-fluorophenyl)-1,3,8-triazaspiro[4.5]decan-4-one (56.8 mg, 0.228 mmol) in DMF (0.5 mL). To the mixture were then added TMOF (0.5 mL) and acetic acid (0.05 mL). The reaction was shaken for 2 hr. Sodium tri(acetoxy) borohydride (60.0 mg, 0.285 mmol) was then added, and the reaction was shaken for 16 hr. The reaction was quenched with 1.0 M of sodium hydroxide aqueous solution (0.5 mL) and the crude products were extracted from the aqueous layers with DCM. The organic solvents were then removed under vacuum. The crude product was purified by the Gilson semi-preparative HPLC to yield the title product as a TFA salt. The HPLC method used gradient flow at 10 mL/min from 10% of acetonitrile(with 0.1% TFA) in water (with 0.1% TFA) to 90% acetonitrile in water(with 0.1% TFA) in 10 min.

Compounds 35, 38, 42, 43, 45, 46 and 47 were similarly prepared according to the procedures above with selection and substitution of a suitably substituted 1,3,8-triazaspiro[4.5]decan-4-one for the 1-(4-fluorophenyl)-1,3,8-triazaspiro[4,5]decan-4-one in Step C.

Compounds 48, 50, 51, 52, 53, 54, 55 and 56 were similarly prepared according to the procedures above reacting 2-(2-furanyl)-benzaldehyde and selection and substitution of a suitably substituted 1,3,8-triazaspiro[4.5]decan-4-one for 1-(4-fluorophenyl)-1,3,8-triazaspiro[4,5]decan-4-one in Step C.

Compounds 60, 61, 62, 63, 64, 66, 67, 68, 69 and 70 were similarly prepared according to the procedure above with selection and substitution of a suitable reagent for the 1-(4-fluorophenyl)-1,3,8-triazaspiro[4,5]decan-4-one in Step C.

EXAMPLE 11

4-oxo-1-phenyl-8-[[2-(2-thienyl)phenyl]methyl]-1,3,8-triazaspiro[4.5]decane-3-acetamide (Compound # 36)

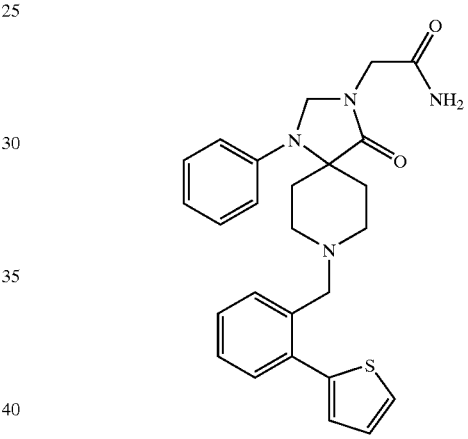

Step A

1-Phenyl-1,3,8-triazaspiro[4.5]decan-4-one (6.8 g, 29.2 mmol) was dissolved in a mixed solvent of anhydrous DCE (100 mL) and NMP (50 mL). To the solution were added 2-(2-thienyl)benzaldehyde (5.0 g, 26.6 mmol), prepared as in Example 10, step A, and acetic acid (1.5 mL). The reaction was stirred for 2 hr. Sodium triacetoxyborohydride (11.3 g, 53.1 mmol) was then added to the reaction mixture. The reaction mixture was stirred for 16 hr, and then stopped by adding saturated NH₄Cl aqueous solution (20 mL). The crude product was extracted from the aqueous layer with ethyl acetate, and the organic layer was dried over MgSO₄. The solvents were removed under vacuum, the resulting white solid was washed with ether and hexane, twice each, to yield the product.

Step B

To a solution of the product from Step A (201 mg, 0.124 mmol) anhydrous NMP (10 mL) was added sodium hydride (7.4 mg, 0.186 mmol), and the reaction was stirred for 1 hr. The reaction was then split into 5 portions. One portion was added to a solution of 2-bromoacetamide (19.7 mg, 0.143 mmol) in NMP (2 mL) the reaction mixture was stirred for 16 hr, and then the reaction was stopped by adding water (2 mL). The product was extracted from the aqueous layer with DCM, the solvents were removed, and the residue purified by the Gilson semi-preparative HPLC to yield the product as a TFA salt. The HPLC method used gradient flow at 10 mL/min from 10% of acetonitrile(with 0.1% TFA) in water (with 0.1% TFA) to 90% acetonitrile in water(with 0.1% TFA) in 10 min.

Compounds 31, 33 and 40 were prepared similarly according to the procedure described above with selection and substitution of suitable alkyl bromides in Step B.

EXAMPLE 12

4-oxo-1-phenyl-8-[[2-(2-thienyl)phenyl]methyl]-1,3,8-triazaspiro[4.5]decane-3-acetic acid (Compound #40)

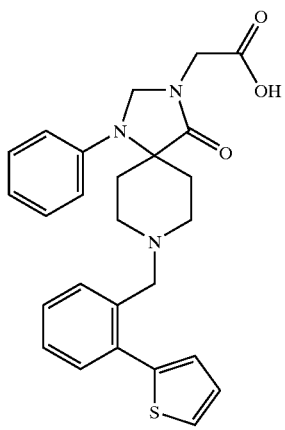

Step A

To a solution of the product prepared in Example 11, Step A (50 mg, 0.124 mmol) in anhydrous NMP (10 mL) was added sodium hydride (7.4 mg, 0.186 mmol), and the reaction was stirred for 1 hr. The reaction was added to a solution of t-butyl 2-bromoacetate (21.1 μL, 0.143 mmol) in NMP (2 mL) to prepare the intermediate compound. The reaction mixture was stirred for 16 hrs and then stopped by adding water (2 mL). The product was extracted from the aqueous layer by DCM, the solvents were removed, and the residue purified by the Gilson semi-preparative HPLC to yield the product as a TFA salt. The HPLC method was gradient flow at 10 mL/min from 10% of acetonitrile(with 0.1% TFA) in water (with 0.1% TFA) to 90% acetonitrile in water(with 0.1% TFA) in 10 min.

Step B

To the product prepared in Step A was added 50% TFA in DCM (3 mL), and the reaction was stirred for 3 hours. The solvents and TFA were removed under vacuum to yield the product as a TFA salt.

Compound 39, was similarly prepared according to the procedure described above with substitution of 2-(2-bromoethoxy)-tetrahydro-2H-pyran in Step A, followed by the de-protection by TFA in Step B to yield the product as a TFA salt.

Compound 34, was similarly prepared according to the procedure described above with substitution of N-(2-bromoethyl)-phthalimide in Step A to yield compound 44, followed by de-protection in Step B to yield the product.

EXAMPLE 13

8-(2-chloro-4-methyl-1-phenyl-2,5-dihydro-1H-pyrazol-3-ylmethyl)-1-phenyl-1,3,8-triazaspiro[4.5]decan-4-one (Compound # 303)

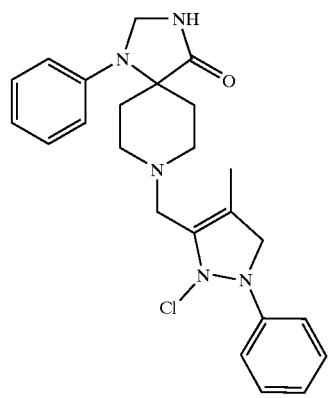

1-Phenyl-1,3,8-triazaspiro[4.5]decan-4-one (0.050 g, 0.216 mmol), 5-chloro-3-methyl-1-phenylpyrazole-4-carboxaldehyde (0.042 g, 0.216 mmol), and sodium triacetoxyborohydride (0.039 g, 0.216 mmol) were combined in dry 1,2-dichloroethane (10 mL). The reaction was stirred overnight at room temperature. The mixture was concentrated to about 1 mL and the residue was purified by preparative thin layer chromatography to yield the title compound as a white solid.

MS (loop pos): $MH^{+}=436.0$.

$^1$H NMR (300 MHz, CDCl$_3$) δ7.21–7.60 (10H, m), 4.73 (2H, s), 3.7 (2H, s), 2.7–2.9 (6H, m), 2.55 (3H, s), 1.70 (2H, d, J=14 Hz).

EXAMPLE 14

8-{2,3'}bithienyl-2'methyl-1-phenyl-1,3,8-triazaspiro[4.5]decan-4-one Acetic Acid Salt (Compound #305)

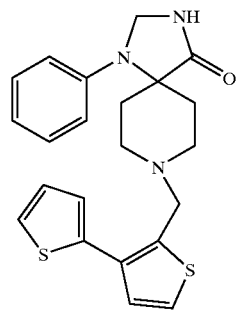

Step A

To a stirring solution of 3-bromo-thiophene-2-carbaldehyde (0.120 g, 0.6 mmol)and 2thiopheneboronic acid (0.134 g, 0.75 mmol) in 1,2-dimethoxyethane(4.0 ml) under argon was added sodium bicarbonate solution (1.0 M, 3.0 ml). Tetrakis(triphenylphosphine) palladium (0) (0.022 g, 0.02 mmol) was then added to the reaction mixture. The solution was heated under reflux for 24 hrs, then was extracted with ethyl acetate three times. The combined organic layers were dried over MgSO$_4$. The solvent was evaporated to yield [2,3']bithiophenyl-2'-carbaldehyde as a colorless oil which was used directly in next step, without further purification.

Step B

To a stirring solution of the crude product from step A were added 1-phenyl-1,3,8-triaza-spiro[4.5]decan-4-one (0.145 g, 0.6 mmol), acetic acid(0.2 ml) in THF (4.0 ml) and sodium triacetoxyborohydride (0.266 g, 1.2 mmol) and the resulting reaction mixture stirred at room temperature overnight. The solution was filtered and purified via HPLC purification to yield the title compound as a white solid.

MS (loop pos): MH$^+$=410.0.

$^1$H NMR (300 MHz, DMSO d$_6$) δ8.98 (s, 1H), 7.88 (d, J=5 Hz, 1H), 7.70 (d, J=5 Hz, 1H), 7.38 (d, J=3 Hz, 1H), 7.33 (d, J=5 Hz, 1H), 7.26–7.20 (m, 3H), 6.92–6.82 (m, 2H), 6.79 (m, 1H), 4.75 (s, 2H), 4.59 (s, 2H), 3.61 (m, 2H), 3.43 (m, 2H), 2.73 (m, 2H), 1.87 (m, 2H).

EXAMPLE 15

8-(2-methyl-4-thein-2-yl-2H-pyrazol-3-ylmethyl)-1-phenyl-1,3,8-triazaspiro[4.5]decan-4-one
(Compound # 304)

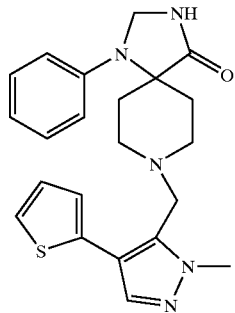

Step A

2-Methyl-4-thien-2-yl-2H-pyrazol-3-carbaldehyde was prepared according to the process described in Step A of Example 14, with substitution of 2-bromo-2-methyl-2H-pyrazol-3-carbaldehyde for 3-bromo-thiophene-2-carbaldehyde. The product was used directly in the next step without purification.

Step B

The title compound was prepared according to the process described in Step B of Example 14, with substitution of 2-methyl-4-thien-2-yl-2H-pyrazol-3-carbaldehyde for [2,3'] bithiophenyl-2'-carbaldehyde:, to yield the title compound as white solid.

MS (loop pos): MH$^+$=408.0.

$^1$H NMR (300 MHz, DMSO d$_6$) δ9.00 (s, 1H), 8.14 (s, 1H), 7.55 (d, J=2 Hz, 1H), 7.26–7.13 (m, 4H), 6.95 (d, J=5 Hz, 2H), 6.81 (m, 1H), 4.60 (s, 2H), 4.47 (s, 2H), 3.93 (s, 3H), 3.69 (m, 2H), 3.54 (m, 2H), 2.80 (m, 2H), 1.89 (m, 2H).

EXAMPLE 16

8-((2-tolyl)-pyridin-3-ylmethyl)-1-phenyl-1,3,8-triazaspiro[4.5]decan-4-one Acetic Acid Salt
(Compound # 306)

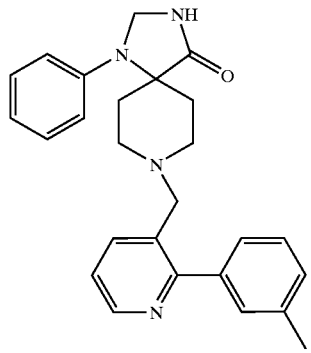

Step A

To a stirring solution of 2-bromopyridine(5.13 g, 3.2 mmol) in THF (90 ml) at −78° C. was slowly added lithium diisopropylamide (LDA) (2 M in THF, 17.9 ml, 3.6 mmol) and the resulting reaction mixture allowed to stir for three hours. To the reaction mixture was then slowly added DMF (9.49 g, 130 mmol) in THF (10 ml). The reaction mixture was stirred at −78° C. for 30 min, and was then allowed to warm to room temperature. Water (100 mol) was added and then the reaction mixture was extracted with ethyl acetate three times. The combined organic layers were dried over MgSO$_4$. The solvent was removed and the resulting residue purified over silica gel chromatography eluted with hexane, to yield 2-bromo-pyridine-3-carbaldehyde as a white solid.

$^1$H NMR (300 MHz, CDCl$_3$) δ10.35(s, 1H), 8.58 (dd, J=2 Hz, 5 Hz, 1H), 8.18 (dd, J=2 Hz, 6 Hz, 1H), 7.44 (dd, J=5 Hz, 6 Hz, 1H).

Step B

To a stirring solution of 2-bromo-pyridine-3-carbaldehyde(0.68 g, 3.6 mmol) were added 1-phenyl-1,3, 8-triazaspiro[4.5]decan-4-one (0.846 g, 3.6 mmol), and acetic acid(1.1 g, 18 mmol) in THF (40.0 ml) and sodium triacetoxyborohydride (1.55 g, 7.3 mmol) and the resulting reaction mixture stirred at room temperature overnight. Water (50 ml) was added and the reaction mixture solution was extracted with ethyl acetate three times. The combined organic layers were dried over MgSO$_4$. The solvent was removed and the resulting residue was purified over silica gel column eluted with methylene chloride (97%), methanol (2%), acetic acid(1%) and then with saturated sodium bicarbonate solution to yield 8-(2-bromo-pyridin-3-ylmethyl)-1-phenyl-1,3,8-triazaspiro[4.5]decan-4-one as a white solid.

MS (loop pos): MH$^+$=402.9.

$^1$H NMR (300 MHz, DMSO d$_6$) d; 8.67 (s, 1H), 8.30 (m, 1H), 7.93 (m, 1H), 7.49 (m, 1H), 7.25 (m, 2H), 6.88 (m, 2H), 6.75 (m, 1H), 4.58 (s, 2H), 3.59 (s, 2H), 2.90–2.53 (m, 6H), 1.61 (m, 2H).

Step C

To a stirring solution of the compound prepared in Step B (0.050 g, 0.12 mmol) and m-tolylboronic acid (0.025 g, 0.18 mmol) in 1,2-dimethoxyethane (3.0 ml) under argon was added sodium bicarbonate solution (1.0 M, 0.3 ml). Tetrakis (triphenylphosphine) palladium (0) (0.007 g, 0.006 mmol) was then added to the reaction mixture. The solution was heated at 91° C. for 24 hrs, the solvent was then evaporated and the resulting residue was purified over HPLC to yield the title compound as a white solid.

MS (loop pos): MH$^+$=413.1.

$^1$H NMR (300 MHz, DMSO d$_6$) δ8.94 (s, 1H), 8.74 (m, 1H), 8.20 (m, 1H), 7.58 (m, 1H), 7.45–7.21 (m, 6H), 6.90–6.79 (m, 3H), 4.56 (s, 2H), 4.46 (s, 2H), 3.30 (m, 4H), 2.66 (m, 2H), 2.30 (s, 3H), 1.82 (m, 2H).

EXAMPLE 17

1-phenyl-8-(2-(3-thienyl)-6-fluorophenyl)methyl-1,3,8-triazaspiro[4.5]decan-4-

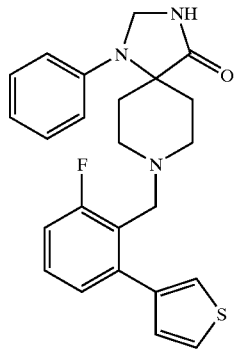

one (Compound # 503)

6-Chloro-2-fluorobenzaldehyde (0.100 g, 0.772 mmol), 3-thienylboronic acid (0.148 g, 1.16 mmol), tris(dibenzylideneacetone)dipalladium(0) (0.018 g, 0.019 mmol), tri-tert-butylphosphine (0.008 g, 0.039 mmol), and potassium fluoride (0.202 g, 3.37 mmol) were dissolved in dry dioxane (4 mL). The reaction mixture was heated to reflux overnight. The reaction mixture was cooled and filtered through a plug of silica, washing with acetone. The filtrate was concentrated and then dissolved in 1,2-dichloroethane (10 mL). Sodium triacetoxyborohydride (0.128 g, 0.849 mmol) and 1-phenyl-1,3,8-triazaspiro[4.5]decan-4-one (0.165 g, 0.772 mmol) were then added. The reaction mixture was stirred overnight at room temperature. The reaction mixture was then diluted with water (15 mL) and extracted with dichloromethane (3×10 mL). The separated organic layers were concentrated and the residue was purified by preparative thin layer chromatography (5% methanol in dichloromethane) to yield the title compound as a yellow amorphous solid.

MS (loop pos): MH$^+$=422.0

$^1$H NMR (CDCl$_3$) δ7.93 (1H, s), 7.79 (1H, s), 7.48 (1H, d, J=4.7 Hz), 7.37 (1H, dd, J=4.8, 3.0 Hz), 7.20–7.31 (3H, m), 7.03 (1H, t, J=8.0 Hz), 6.80–6.90 (4H, m), 4.74 (2H, s), 3.52 (2H, s), 2.63–2.96 (8H, m), 1.71 (2H, d, J=13.7 Hz).

Compound 501, 502, 504 and 505 were similarly prepared according to the procedure described above with selection and substitution of a suitable boronic acid for the 3-thienyl boronic acid.

EXAMPLE 18

8-(2-(2-Biphenyloxy)ethyl)-1-phenyl-1,3,8-triazaspiro[4.5]decan-4-one

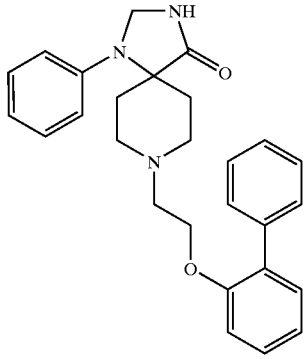

(Compound # 406)

1-Phenyl-1,3,8-triazaspiro[4.5]decan-4-one (0.250 g, 1.08 mmol), 2-chloroacetaldehyde (45% solution in water, 0.283 mg, 1.62 mmol) and sodium cyanoborohydride (0.103 g, 1.62 mmol) were combined in methanol (5 mL). The reaction mixture was stirred at room temperature overnight. The reaction mixture was then concentrated and the residue purified by column chromatography (5% methanol in dichloromethane). A portion of the resulting product (0.025 g, 0.085 mmol) was dissolved in dry dimethylformamide (1 mL). 2-Hydroxybiphenyl (0.029 g, 0.170 mmol) and potassium carbonate (0.059 g, 0.425 mmol) were then added. The reaction mixture was stirred at room temperature overnight, diluted with water (5 mL), and then extracted with dichloromethane (3×5 mL). The combined extracts were concentrated and the residue was purified by preparative thin layer chromatography (5% methanol in dichloromethane) to yield the title product as a white amorphous solid.

MS: 428.1 (M+1)

$^1$H NMR (CDCl$_3$) δ7.58–7.60 (2H, m), 7.24–7.39 (7H, m), 7.00–7.06 (2H, m), 6.83–6.91 (3H, m), 6.39 (1H, s), 4.72 (1H, s), 4.12 (2H, t, J=5.7 Hz), 2.78–2.96 (6H, m), 2.59–2.69 (2H, m), 1.67 (2H, d, J=14.0 Hz).

EXAMPLE 19

8-(2-phenoxy-benzyl)-1-phenyl-1,3,8-triazaspiro[4.5]decan-4-one HCl Salt (Compound # 57)

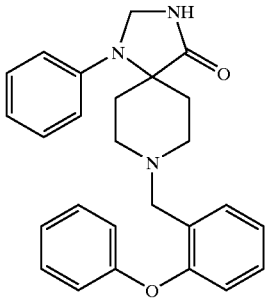

Step A (Yaeger, et al. *Synthesis*, 1995, pp28)

To a solution of phenol (1.8888 g, 0.0201 mol) and 2-fluorobenzaldehyde (2.14 mL, 0.0203 mol) in N,N-dimethylacetamide (20 mL) was added anhydrous K$_2$CO$_3$ (3.0798 g, 0.0223 mol). The resulting heterogenous mixture was refluxed for 3 h. The resulting green mixture was then treated with H₂O (100 mL) and extracted with EtOAc (2×100 mL). The combined organic extracts were washed with H₂O (4×100 mL), dried over Na₂SO₄, filtered and concentrated. The resulting dark residue was purified by flash chromatography on silica gel (10% EtOAc in hexane) to yield 2-phenoxybenzaldehyde as a light yellow oil.

¹H NMR (300 MHz, DMSO d₆) δ6.91 (m, 1H), 7.15 (m, 2H), 7.19–7.25 (m, 2H), 7.45–7.55 (m, 2H), 7.65–7.70 (m, 1H), 7.85–7.90 (m, 1H).

Step B

To a mixture of 1-phenyl-1,3,8-triazaspiro[4.5]decan-4-one (291 mg, 1.26 mmol) and 2-phenoxybenzaldehyde (299 mg, 1.50 mmol) in 1,2-dichloroethane (25 mL) was added sodium triacetoxyborohydride (454 mg, 2.14 mmol). The resulting mixture was stirred at room temperature under nitrogen atmosphere for 20 h. The reaction mixture was then quenched with 1N aqueous NaHCO₃ and extracted with CHCl₃ (100 mL). The combined extracts were dried over Na₂SO₄, filtered and concentrated. The isolated solid was purified by flash chromatography on silica gel to yield the title compound as a free base.

The free base was dissolved in CHCl₃ (35 mL), and treated with 2.5 mL of 1 N HCl in Et₂O. The corresponding HCl salt was precipitated by addition of Et₂O, then collected by filtration and dried the vacuum oven at 50° C. for 18 h to yield the title product as an amorphous solid.

MS (loop pos): MH⁺=414.1 (100%).

¹H NMR (300 MHz, DMSO d₆) δ1.85–1.95 (m, 1H), 2.90–3.10 (m, 2H), 3.35–3.60 (m, 2H), 3.70–3.85 (m, 2H), 4.35–4.45 (m, 2H), 4.60 (s, 2H), 7.05–7.20 (m, 4H), 7.25–7.35 (m, 4H, 7.45–7.55 (m, 3H), 7.85–7.90 (m, 1H), 9.00 (s, 1H), 10.9 (s, 1H)

EXAMPLE 20

8-[3-(2-thiophen-2-yl-phenyl)-propyl-1-phenyl-1,3, 8-triazaspiro[4.5]decan-4-one HCl Salt (Compound # 403)

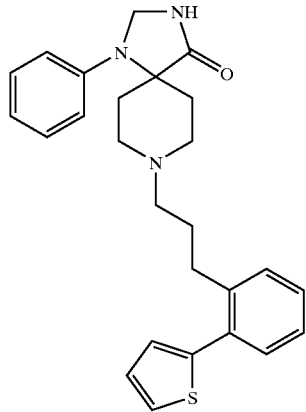

Step A

Trimethylsilyldiazomethane (2M in hexanes, 5.0 mL, 10.0 mmol) was added to a solution of 3-(2-bromophenyl) propionic acid (1.376 g, 6.00 mmol) in anhydrous benzene (28 mL) and anhydrous methanol (8 mL). The reaction mixture was stirred at room temperature for 2 h, and then the volatiles were removed in vacuo, to yield crude methyl 3-(2-bromophenyl)propionate which was carried forward without further purification.

¹H NMR (300 MHz, DMSO d₆) δ2.39 (t, 7.55, 7.55 Hz, 2H), 2.72 (t=7.55, 7.55 Hz, 2H), 3.36 (s, 3H), 6.89–6.96 (m, 1H), 7.05–7.14 (m, 2H), 7.34–7.37 (m, 1H).

Step B

To a mixture of the crude methyl 3-(2-bromophenyl) propionate (1.59 g, ca 0.006 mol) and tetrakis (triphenylphosphine) palladium (0) (695 mg, 0.601 mmol) in 1,2-dimethoxyethane (45 mL) were added thiophene-2-boronic acid (2.304 g, 0.018 mol) and 1N aqueous NaHCO₃ (15 mL). The resulting mixture was heated at reflux under nitrogen atmosphere for 66 hrs. The dark reaction mixture was then diluted with water (100 mL) and extracted with EtOAc (2×100 mL). The combined organic layers were dried over Na₂SO₄, filtered and then concentrated. The resulting crude product was purified by flash chromatography (5% EtOAc in hexane) to yield methyl 2-(2-thienyl) phenylpropionate as a light green oil.

¹H NMR (300 MHz, DMSO d₆) δ2.50–2.56 (m, 2H), 2.95–2.98 (m, 2H), 3.55 (s, 3H), 7.14–7.17 (m, 2H), 7.27–7.35 (m, 4H), 7.61–7.63 (m, 1H).

Step C

To a cold (0° C.) solution of methyl 2-(2-thienyl) phenylpropionate (387 mg, 1.57 mmol) and anhydrous lithium chloride (353 mg, 8.32 mmol) in an EtOH/THF mixture (4:3; 28 mL) was added sodium borohydride (315 mg, 8.32 mmol). The reaction mixture was then stirred at room temperature for 20 h. Aqueous NH₄Cl (50 mL) was added and the crude product was extracted with EtOAc (2×50 mL). The organic layer was separated, dried over Na₂SO₄, filtered and concentrated. The resulting residue was purified by flash chromatography (5% EtOAc in hexane) to yield 2-(2-thienyl)phenpropyl alcohol as a light yellow oil.

¹H NMR (300 MHz, DMSO d₆) δ1.59–1.68 (m, 2H), 2.69–2.74 (m, 2H), 3.34–3.38 (t, J=6.6, 6.6 Hz, 2H), 4.01–4.06 (br s, 1H), 7.12–7.34 (m, 6H), 7.59–7.61 (m, 1H).

Step D

To a cold (0° C.) solution of 2-(2-thienyl)phenpropyl alcohol (312 mg, 1.43 mmol) and triethylamine (250 μL, 1.79 mmol) in anhydrous CH₂Cl₂ (10 mL) was added methanesulfonyl chloride (120 μL, 1.55 mmol). Upon complete addition of the methanesulfonyl chloride, the reaction was stirred at room temperature under argon atmosphere for 1 h. The reaction mixture was then diluted with CH₂Cl₂ (75 mL), washed with H₂O (2×50 mL), aq NaHCO₃ (2×25 mL), dried over Na₂SO₄, filtered and concentrated to yield 3-(2-thien-2-yl-phenyl)-propyl ester methanesulfonic acid as a yellow oil, which was taken into the next step without further purification.

¹H NMR (300 MHz, CDCl₃) δ1.90–1.99 (m, 2H), 2.84–2.90 (m, 2H), 2.93 (s, 3H), 4.15 (t, J=6.37, 6.37 Hz), 7.00–7.02 (m, 1H), 7.07–7.10 (m, 1H), 7.21–7.38. (m, 5H).

Step E

The crude oil prepared in Step D (397 mg, 1.34 mmol), 1-phenyl-1,3,8-triazaspiro[4.5]decan-4-one (295 mg, 1.28 mmol) and diisopropylethylamine (200 μL, 1.55 mmol) in 1-methyl-2-pyrrolidinone (4 mL) were stirred in an preheated oil bath (65° C.) for 18 h. The reaction mixture was diluted with aq NaCl and extracted with EtOAc (2×40 mL). The organic solution was washed with H₂O (4×50 mL), dried over Na₂SO₄, filtered and concentrated. The resulting crude product was purified by tapered preparative TLC (4% MeOH in CHCl₃) to furnish 239 mg of a beige solid. The free base was dissolved in CHCl₃ (25 mL), and then treated with 1 mL of 1 N HCl in Et₂O. The HCl salt was precipitated by addition of Et₂O, collected by filtration and dried in the vacuum oven at 60° C. for 20 h to yield the title product as an amorphous beige solid.

MS (loop pos): MH⁺=432.1 (100%)

¹H NMR (300 MHz, DMSO d₆) δ1.75–1.85 (m, 2H), 1.90–2.05 (m, 2H), 2.75–2.80 (m, 2H), 2.85–2.95 (m, 2H), 2.95–3.10 (m, 2H), 3.40–3.60 (m, 4H), 4.62 (s, 2H), 6.78–6.82 (m, 1H), 7.01–7.05 (m, 2H), 7.18–7.43 (m, 8H), 7.60–7.70 (m, 1H), 9.02 (s, 1H), 10.46 (br s, 1H exchangeable).

Compound 404 was similarly prepared according to the procedure described above with substitution of thiophene-3-boronic acid for the thiophene-2-boronic acid in Step A.

EXAMPLE 21

8-[4-(2-thiophen-2-yl-phenyl)-butyl]-1-phenyl-1,3,8-triazaspiro[4.5]decan-4-one HCl Salt (Compound # 405)

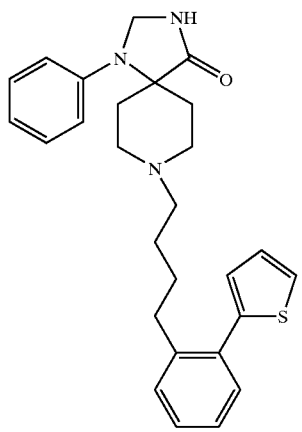

Step A
(Ref: Wolfe, et al; Tetrahedron, 1996, 52(21), 7525)

To an ice cold solution of 2-bromobenzyl bromide (5.00 g, 0.020 mol) in THF (25 mL) was added 1M allyl magnesium bromide (100 mL, 0.100 mol) slowly via cannula. The reaction mixture was stirred at reflux for 1.5 h, cooled in an ice bath and quenched with 50 mL of aqueous 2M $H_2SO_4$. Water (50 mL) was added to dissolve any remaining solid and the layers were separated. The aqueous layer was extracted with $Et_2O$ (2×150 mL). The combined organic extracts were dried over $Na_2SO_4$, filtered and concentrated to yield 1-bromo-2-but-3-enyl-benzene as a light yellow oil. The isolated crude product was carried forward without further purification.

$^1$H NMR (300 MHz, CDCL$_3$) δ2.33–2.40 (m, 2H), 2.80–2.85 (m, 2H), 4.98–5.17 (m, 2H), 5.81–5.94 (m, 1H), 7.02–7.08 (m, 1H), 7.19–7.27 (m, 2H), 7.51–7.54 (m, 1H).

Step B

To a solution of 0.4 M 9-BBN in hexane (72 mL, 28.8 mmol) was added 4-bromophenyl-1-butene (3.99 g, 18.9 mmol) at room temperature. The resulting mixture was stirred at room temperature for 20 h. The mixture was treated sequentially with 3.3 mL of 6N aqueous NaOH (19.8 mmol), THF (7 mL), and 30% $H_2O_2$ in $H_2O$ (7 mL), then refluxed for 2 h. The reaction mixture was then cooled to room temperature. The organic layer was washed with aqueous sodium sulfite (40 mL), $H_2O$ (20 mL), and brine (20 mL). The aqueous extracts were combined, saturated with solid $K_2CO_3$ and extracted with $Et_2O$ (3×50 mL). The combined organic extracts were dried over $Na_2SO_4$, filtered and concentrated. The resulting crude product was purified by flash chromatography twice (33% EtOAc in hexane and 20% EtOAc in hexane) to yield 4-(o-bromophenyl)butanol).

$^1$H NMR (300 MHz, DMSO-d$_6$) δ1.41–1.64 (m, 4H), 2.69 (t, =7.28, 7.61 Hz, 2H), 3.42 (t, J=6.40, 6.41 Hz, 2H), 4.40 (br s, 1H), 7.10–7.16 (m, 1H), 7.30–7.33 (m, 2H), 7.55–7.57 (m, 1H).

Step C

To a solution of 4-(o-bromophenyl)-1-butanol (1.222 g, ca 0.0053 mol) and tetrakis(triphenylphosphine) palladium (0) (650 mg, 0.562 mmol) in 1,2-dimethoxyethane (55 mL) was added thiophene-2-boronic acid (2.057 g, 0.016 mol) and 1N aqueous NaHCO$_3$ (15 mL). The resulting mixture was heated at reflux under nitrogen atmosphere for 3 days. The dark reaction mixture was diluted with water (50 mL) and extracted with EtOAc (100 mL). The organic layer was dried over $Na_2SO_4$, filtered through a bed of Celite and concentrated to yield a crude which was purified by flash chromatography (30% EtOAc in hexane) to yield 4-(2-thien-2-yl-phenyl)-butan-1-ol as a light brown oil.

$^1$H NMR (300 MHz, DMSO d$_6$) δ1.37–1.56 (m, 4H), 2.66–2.71 (m, 2H), 3.31–3.35 (m, 2H), 4.33 (br s, 1H), 7.10–7.15 (m, 2H), 7.21–7.26 (m, 1H), 7.31–7.34 (m, 3H), 7.59–7.61 (m, 1H).

Step D

To a cold (0° C.) solution of 2-(2-thienyl)phenylbutanol (1.149 g, 0.00495 mmol) and triethylamine (0.87 mL, 6.24 mmol) in anhydrous $CH_2Cl_2$ (40 mL) was added methanesulfonyl chloride (0.48 mL, 6.20 mmol). Upon complete addition of the methanesulfonyl chloride, the reaction was stirred at room temperature under argon atmosphere for 1.5 h. The reaction mixture was then diluted with $CH_2Cl_2$ (50 mL), washed with $H_2O$ (3×50 mL), dried over $Na_2SO_4$, filtered and concentrated to yield crude 4-(2-then-2-yl-phenyl)-butyl ester methane sulfonic acid as a brown oil, which was taken into the next step without further purification.

$^1$H NMR (300 MHz, CDCl$_3$) δ1.66–1.76 (m, 4H), 2.77 (t, J=7.1, 7.4 Hz, 2H), 2.94 (s, 3H), 4.15 (t, J=6.08, 6.08 Hz), 7.00–7.02 (m, 1H), 7.07–7.10 (m, 1H), 7.25–7.35. (m, 5H).

Step E

The crude oil from Step D (390 mg, 1.24 mmol), 1-phenyl-1,3,8-triazaspiro[4.5]decan-4-one (231 mg, 1.00 mmol) and diisopropylethylamine (210 µL, 1.20 mmol) in 1-methyl-2-pyrrolidinone (2.5 mL) were stirred in an preheated oil bath (70° C.) for 20 h. The reaction mixture was diluted with aq NaCl (25 mL) and extracted with EtOAc (2×20 mL). The organic layer was washed with $H_2O$ (4×50 mL), dried over $Na_2SO_4$, filtered and concentrated to yield a crude oil, which was purified by flash chromatography (5% $CH_3OH$ in CHCl$_3$) to yield the title compound as a free base, as an oil (218 mg). The free base was dissolved in CHCl$_3$ (15 mL), and treated with 1 mL of 1 N HCl in $Et_2O$. The HCl salt was precipitated by addition of $Et_2O$, collected by filtration and dried in the vacuum oven at 50° C. for 20 h to yield the title product as an amorphous beige solid.

MS (loop pos): MH$^+$=446.1 (100%)

$^1$H NMR (300 MHz, DMSO d$_6$) δ1.75–1.85 (m, 2H), 1.90–2.05 (m, 2H), 2.75–2.80 (m, 2H), 2.85–2.95 (m, 2H), 2.95–3.10 (m, 2H), 3.40–3.60 (m, 4H), 4.62 (s, 2H), 6.80–6.90 (m, 1H), 7.01–7.05 (m, 2H), 7.18–7.43 (m, 8H), 7.6–7.65 (m, 1H), 9.00 (s, 1H), 10.60 (br s, 1H exchangeable).

Compound 506 was similarly prepared according to the procedure described above with substitution of 1-(4-fluorophenyl)-1,3,8-triazaspiro[4.5]decan-4-one for the 1-phenyl-1,3,8-triazaspiro[4.5]decan-4-one in Step E.

EXAMPLE 22

5-[4-oxo-1-phenyl-8-(2-thionphen-3-yl-benzyl)-1,3,8-triazaspiro[4.5]dec-3-ylmethyl]-oxazole-4-carboxylic acid methyl ester HCl Salt (Compound # 65)

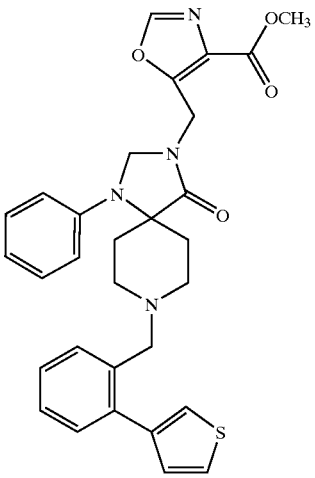

Step A

To a cold (0° C.) mixture of Boc 3-carboxymethyl-1-phenyl-1,3,8-triazaspiro[4.5]decan-4-one (3.893 g, 0.010 mol), and potassium carbonate sesquihydrate (6.606 g, 0.040 mol) in DMF (20 mL) was added diphenylphosphoryl azide (3.03 mL, 14.0 mmol) and methyl isocyanoacetate (1.9 mL, 20.9 mmol). The reaction mixture was stirred for 1 day at room temperature. The reaction was then diluted with aq NaCl and extracted with $CHCl_3$ (150 mL). The organic solution was dried over $Na_2SO_4$, filtered and concentrated to a brown oil. The crude product was purified by flash chromatography twice (2% MeOH in $CHCl_3$) to yield 3-(4-methoxycarbonyl-oxazol-5-ylmethyl)-4-oxo-1-phenyl-1,3,8-triazaspiro[4.5]decane-8-carboxylic acid-t-butyl ester as a tacky solid.

$^1$H NMR (300 MHz, $CDCl_3$) δ1.50 (s, 9H), 1.62–1.66 (m, 2H), 2.40–2.60 (m, 2H), 3.50–3.65 (m, 2H), 3.98 (s, 3H), 3.98–4.18 (m, 2H), 5.07 (s, 2H), 6.72–6.75 (m, 2H), 6.85–6.90 (m, 1H), 7.21–7.24 (m, 2H), 7.89 (s, 1H).

Step B

To a solution of the solid prepared in Step A (1.9457 g, 0.00414 mol) in DCM (35 mL) was added $CF_3CO_2H$ (15 mL). The reaction mixture was then stirred for 1.5 h and concentrated in vacuo. The residue was treated with aqueous $NaHCO_3$ and product was extracted into $CHCl_3$ (2×75 mL). The organic extracts were dried over $Na_2SO_4$, filtered and concentrated to yield an oil. The oil (the free base of 1-phenyl-3-(4-methoxycarbonyl-oxazol-5-ylmethyl)-1,3,8-triazaspiro[4.5]decan-4-one) was dissolved in EtOAc (30 mL), and treated with 7 mL of 1N HCl in $Et_2O$. The HCl salt was precipitated by addition of $Et_2O$, collected by filtration and dried in the vacuum oven at 50° C. for 20 h to yield an amorphous beige solid.

MS (loop pos): $MH^+$=371.1 (100%).

$^1$H NMR (300 MHz, DMSO $d_6$) δ1.75–1.85 (m, 2H), 2.45–2.55 (m, 2H), 3.30–3.40 (m, 2H), 3.45–3.60 (m, 2H), 3.85 (s, 3H), 4.70 (s, 2H), 4.95 (s, 2H), 6.75–6.85 (m, 1H), 6.90–7.00 (m, 2H), 7.20–7.25 (m, 2H), 8.45 (s, 1H), 8.90–9.20 (m, 2H-exchangeable).

Step C

A heterogenous mixture of 2-(2-thienyl)benzaldehyde (206 mg 1.09 mmol), the HCl salt prepared in Step B (406 mg, 1.00 mmol) and triethylamine (0.21 mL, 1.50 mmol) in 1,2-dichloroethane (10 mL) was stirred for 0.5 h, treated with sodium triacetoxyborohydride (372 mg, 1.76 mmol) and the resulting mixture stirred for 1.5 days. The reaction mixture was then quenched with 1N aqueous $NaHCO_3$ and extracted with $CHCl_3$ (2×50 mL). The combined extracts were dried over $Na_2SO_4$, filtered and concentrated to yield a solid. The isolated solid was purified by flash chromatography on silica gel (3% MeOH in $CHCl_3$) to yield 1-phenyl-3-(4-methoxycarbonyl-oxazol-5-ylmethyl)-8-(2-thien-2-yl-phenylmethyl)-1,3,8-triazaspiro[4.5]decan-4-one as a free base. The free base (180 mg) was dissolved in EtOAc (25 mL) and treated with 0.7 mL of 1N HCl in $Et_2O$. HCL salt was precipitated by addition of $Et_2O$, collected by filtration and dried the vacuum oven at 50° C. for 18 h to yield the title compound as an amorphous solid.

MS (loop pos): $MH^+$=543.6 (100%). $^1$H NMR (300 MHz, DMSO $d_6$) δ1.75–1.85 (m, 2H), 2.45–2.55 (m, 2H), 3.30–3.40 (m, 2H), 3.45–3.60 (m, 2H), 3.85 (s, 3H), 4.70 (s, 2H), 4.95 (s, 2H), 6.70–6.80 (m, 1H), 6.90–7.00 (m, 2H), 7.15–7.25 (m, 4H), 7.45–7.60 (m, 3H), 7.70–7.75 (m, 1H), 8.15–8.20 (m, 1H), 8.45 (s, 1H), 10.9 (br s, 1H-exchangeable).

EXAMPLE 23

3-(2-dimethylamino-ethyl)-1-phenyl-8-[2-(2-thiophen-2-yl-phenyl)-ethyl]-1,3,8-triazaspiro[4.5]decan-4-one HCl Salt (Compound # 407)

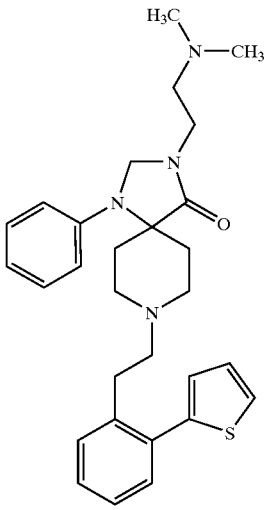

To a heterogenous mixture of unwashed 60% NaH dispersed in mineral oil (96.5 mg, 2.41 mmol) in DMF (3 mL) was added 8-[2-[2-(2-thienyl)phenyl]ethyl]-1-phenyl-1,3,8-triazaspiro[4.5]decan-4-one (prepared as in Example 5) (208.8 mg, 0.500 mmol). The mixture was stirred until $H_2$ gas evolution was observed to stop (30 min), then treated with N,N-dimethylaminoethyl chloride hydrochloride (158 mg, 1.10 mmol). The resulting reaction mixture was stirred for an additional 18 h under argon atmosphere. The reaction was quenched with aqueous $NH_4Cl$ (50 mL), and the crude product was extracted into $CHCl_3$ (2×40 mL). The organic extracts were washed with $H_2O$ (5×50 mL), dried over $Na_2SO_4$, filtered and concentrated to a crude oil. The crude oil was washed with hexane (3×50 mL) to remove mineral oil, then purified by Tapered prep TLC (6% MeOH in $CHCl_3$) to yield title compound as a free base. The free base was dissolved in $CHCl_3$ (15 mL) and treated with 1.0 mL of 1N HCl in Et₂O. HCL salt was precipitated by addition of Et₂O, collected by filtration and dried in the vacuum oven at 60° C. for 18 h to yield the title compound as a white amorphous solid.

MS (loop pos): MH⁺=498.2 (100%)

¹H NMR (300 MHz, DMSO d₆) δ2.05–2.15 (m, 2H), 2.75 (s, 6H), 2.80–2.95 (m, 2H), 3.25 (s, 2H), 3.30–3.45 (m, 4H), 3.50–3.65 (m, 4H), 3.65–3.75 (m, 2H), 4.75 (s, 2H), 6.78–6.82 (m, 1H), 7.01–7.05 (m, 2H), 7.18–7.29 (m, 4H), 7.33–7.43 (m, 3H), 7.66–7.68 (m, 1H), 9.02 (s, 1H), 10.70 (br s, 1H exchangeable), 10.90 (br s, 1H exchangeable).

Compounds 408, 409 and 410 were similarly prepared according to the procedure described above with selection and substitution of a suitably substituted reagent for the N,N-dimethylaminoethyl chloride hydrochloride.

EXAMPLE 24

Method for measuring affinity for the ORL-1 receptor

The nociceptin receptor binding assay measures the binding of $^{125}$I-Tyr$^{14}$-nociceptin (2200 Ci/mmol, New England Nuclear) to human nociceptin receptor (ORL-1) on HEK293 cell membranes.

HEK293 cell membrane (prepared as described in Pulito, V. L. et al., 2000, *J. Pharmacol. Exp. Ther.* 294, 224–229), with the exception that the buffer used was a mixture of 50 mM Tris-Cl pH 7.8, 5 mM MgCl₂ and 1 mM EGTA), was added to PEI treated WGA FlashPlates (New England Nuclear) at 1 μg/well in binding buffer of 50 mM Tris-Cl pH 7.8, 5 mM MgCl₂ and 1 mM EGTA. $^{125}$I-Tyr$^{14}$-nociceptin was added at a final concentration of 0.5 nM and the volume adjusted to 50 μl with binding buffer. The plate was incubated for two hours at room temperature, the reactions were aspirated and the wells washed two times with 200 μl binding buffer and then filled with 200 μl binding buffer. The plates were then sealed and counted on a Packard Top Count to determine radioactivity bound to the membranes.

For each test compound, the total binding (%Inh) was measured at several concentrations and the IC₅₀ (the concentration at which 50% of the binding is inhibited) was determined from the graphical display of X=logarithm of concentration versus Y=response, using the following calculation:

$$Y = (\text{Minimum}) + \frac{(\text{Maximum} - \text{Minimum})}{(1 + 10^{\log(EC_{50} - X)})}$$

The ability of selected compounds of the present invention to bind to the ORL-1 receptor in a HEK cell line using a radio-labelled nociceptin as the displacable ligand was determine according to the procedure described above with results as listed in Table 11.

TABLE 11

| Cmpd # | IC₅₀ (μM) | % Inh @ 100 μM | % Inh @ 10 μM |
|---|---|---|---|
| 1 | 0.024 | | |
| 2 | 0.012 | | |
| 3 | 0.960 | | |
| 4 | 0.190 | | |
| 5 | 0.305 | | |
| 6 | 0.058 | | |
| 7 | 0.271 | | |
| 8 | 0.005 | | |
| 9 | 0.006 | | |
| 10 | 0.007 | | |

TABLE 11-continued

| Cmpd # | IC₅₀ (μM) | % Inh @ 100 μM | % Inh @ 10 μM |
|---|---|---|---|
| 11 | 0.054 | | |
| 12 | >10 | insoluble | insoluble |
| 13 | 0.759 | | |
| 14 | 0.866 | | |
| 15 | >10 | 31 | 28 |
| 16 | 0.603 | | |
| 17 | >10 | 19.5 | 24 |
| 18 | 1.3 | | |
| 19 | >10 | 22 | 14.5 |
| 20 | >10 | 25 | 15.5 |
| 21 | >10 | 47 | 43 |
| 22 | 1.100 | | |
| 23 | 0.158 | | |
| 24 | 0.032 | | |
| 25 | 0.201 | | |
| 26 | 3.200 | | |
| 27 | 0.378 | | |
| 28 | 1.300 | | |
| 29 | 0.047 | | |
| 30 | 2.700 | | |
| 31 | 0.0025 | | |
| 32 | 0.0082 | | |
| 33 | 0.0080 | | |
| 34 | 0.0312 | | |
| 35 | 0.0048 | | |
| 36 | 0.0024 | | |
| 38 | 0.0057 | | |
| 39 | 0.0011 | | |
| 40 | 0.0010 | | |
| 41 | 0.0084 | | |
| 48 | 0.0031 | | |
| 49 | 0.0012 | | |
| 50 | 0.0081 | | |
| 51 | 0.0026 | | |
| 52 | 0.0201 | | |
| 53 | 0.0303 | | |
| 57 | 0.0085 | | |
| 58 | 0.524 | | |
| 59 | >10 | | |
| 60 | 0.061 | | |
| 61 | 0.109 | | |
| 62 | 0.025 | | |
| 63 | 0.016 | | |
| 64 | 2.38 | | |
| 65 | 0.0072 | | |
| 66 | 0.048 | | |
| 67 | 0.155 | | |
| 68 | 0.023 | | |
| 69 | 0.043 | | |
| 70 | 1.59 | | |
| 101 | 0.348 | | |
| 102 | 0.632 | | |
| 103 | 0.608 | | |
| 104 | 0.244 | | |
| 105 | 0.761 | | |
| 106 | 4.100 | | |
| 107 | 0.264 | | |
| 108 | 0.574 | | |
| 109 | 1.110 | | |
| 110 | 0.346 | | |
| 111 | 0.786 | | |
| 112 | 0.241 | | |
| 113 | 0.750 | | |
| 114 | 0.339 | | |
| 115 | 2.700 | | |
| 116 | 2.200 | | |
| 117 | 3.49 | | 52 |
| 118 | 0.83 | | |
| 119 | >10 | | 33 |
| 120 | >10 | | 11 |
| 121 | >10 | | 28 |
| 122 | 1.7 | | |
| 123 | 1.23 | | |
| 124 | 0.61 | | |
| 125 | 0.34 | | |
| 201 | >10 | | 13 |
| 202 | 0.388 | | |

TABLE 11-continued

| Cmpd # | IC$_{50}$ ($\mu$M) | % Inh @ 100 $\mu$M | % Inh @ 10 $\mu$M |
|---|---|---|---|
| 203 | 0.484 | | |
| 204 | 0.252 | | |
| 205 | 0.362 | | |
| 206 | 1.140 | | |
| 207 | 0.258 | | |
| 208 | 0.383 | | |
| 209 | 0.194 | | |
| 210 | 0.223 | | |
| 211 | >10 | | 30 |
| 213 | >10 | | 0 |
| 214 | >10 | | 16 |
| 215 | >10 | | 17 |
| 216 | 1.9 | | |
| 217 | 1.8 | | |
| 218 | 1.63 | | |
| 301 | 0.433 | | |
| 302 | 0.133 | | |
| 303 | 4.75 | | |
| 304 | 0.300 | | |
| 305 | 0.011 | | |
| 306 | 0.593 | | |
| 401 | 0.009 | | |
| 402 | 0.0076 | | |
| 403 | 0.003 | | |
| 404 | 0.011 | | |
| 405 | 0.11 | | |
| 406 | 0.94 | | |
| 407 | 0.014 | | |
| 408 | 0.022 | | |
| 409 | 0.012 | | |
| 410 | 0.079 | | |
| 411 | 0.338 | | |
| 412 | 0.790 | | |
| 501 | 0.021 | | |
| 502 | 1.3 | 64 | |
| 503 | 0.013 | | |
| 504 | 0.006 | | |
| 505 | 0.008 | | |
| 506 | 0.74 | | |

EXAMPLE 25

In Vivo Acute Pain/Mouse Abdominal Irritant Test (MAIT)

The procedure used in detecting and comparing the analgesic activity of test compounds for which there is a good correlation with human efficacy is the prevention of acetylcholine-induced abdominal constriction in mice (H. Collier, et al., Br. J. Pharmacol., 1968, 32, 295).

More specifically, male CD1 mice (weighing from 18–24 g) are utilized in determining the analgesic effect of test compounds. The mice are dosed orally with test compound dissolved in distilled water or dissolved in a suspension of 0.5% hydroxypropyl methylcellulose in distilled water. The dosing volume is 2 mL/kg.

The mice are injected intraperitoneally with a challenge dose of acetylcholine bromide. The acetylcholine is completely dissolved in distilled water at a concentration of 5.5 mg/kg and injected at the rate of 0.20 mL/20 g. For scoring purposes, an "abdominal constriction" is defined as a contraction of the abdominal musculature accompanied by arching of the back and extension of the limbs. The mice are observed for 10 minutes for the presence or absence of the abdominal constriction response beginning immediately after receiving the acetylcholine dose, administered at a certain time after the oral administration of test compound. Each mouse is used only once.

The absence of the abdominal constriction response is interpreted as efficacy of the test compound in controlling acute pain.

EXAMPLE 26

In Vivo Study—Carrageenan Paw Hyperalgesia Test

The procedure used in detecting and comparing the anti-inflammatory activity of test compounds is the carrageenan paw hyperalgesia test (Dirig, et al., J. Pharmacol. Expt. Therap., 1998, 285, 1031).

More specifically, male, Sprague-Dawley rats (Charles River Laboratories) are housed in a climate-controlled, virus free environment for at least 5 days prior to testing. Food and water are available ad libitum up to test time.

Test rats are immunized by injecting an irritant (e.g., 0.1 ml of a 0.3–1.0% carrageenan solution in 0.9% saline) subcutaneously into the subplantar tissue of one of the hind paws to stimulate an acute inflammatory reaction. Control rats receive a similar saline injection.

The rats are dosed orally with test compound or vehicle, dissolved in either distilled water or dissolved in a suspension of 0.5% hydroxypropyl methylcellulose in distilled water at a fixed time following carrageenan injection. The dosing volume is 2 mL/kg. The hyperalgesic response of the animal is subsequently evaluated at a fixed later time.

Hyperalgesia is assessed by measurement of a response to a thermal or a mechanical stimulus. Measurement of thermal hyperalgesia is made with a standard laboratory hot plate apparatus, whose surface temperature is precisely determined and evenly maintained. Alternatively, hyperalgesia is evaluated with a commercially available Hargreaves apparatus which selectively elevates the temperature of an individual paw (Dirig, et al., J. Neurosci. Methods, 1997, 76, 183). With either apparatus, hyperalgesia is measured as a reduced latency to response compared to the latency of an untreated or vehicle treated animal, and the analgesic effect of the test compound is seen as a (partial) restoration of the latency toward normal (Dirig, et al., J. Pharmacol. Expt. Therap., 1998, 285, 1031). A response is defined as any shaking, licking, or tucking of the treated paw.

Assessment of hyperalgesia by a mechanical means is effected with a device designed to apply a precisely calibrated force to the paw. Hyperalgesia is measured as reduction in the force, measured in grams, needed to elicit paw withdrawal or vocalization (Randall and Selitto, Arch. Int. Pharmacodyn., 1957, 4, 409). The analgesic effect of the test compound is seen as a (partial) restoration of the force eliciting a response toward normal.

EXAMPLE 27

In vivo Study—Open Space Trait Anxiety (Elevated Plus-Maze or EPM)

This behavioral assay is based on an innate behavior of the animal and may model human anxiety traits. Specifically, this test is based on the innate fear or aversion that rats have of illuminated open spaces. Compounds with anxiolytic activity have been shown to increase the frequency with which rats venture into open spaces and to increase the time the animal spends in the open arm of the EPM (Pellow et al., 1985).

Method

Test compound or vehicle is administered orally to adult rats that have been deprived of food but not water for 18 h before use. At a specified time after dosing, the rats are placed on an open arm of the elevated plus-maze (p-maze), facing the center. The 10-min test is initiated when the rat enters the center of the apparatus. Each black plastic maze has two open arms and two arms with 40 cm high walls (enclosed arms) of equal length (50 cm) extending from the center at right angles, such that arms of similar type are opposite each other. Each p-maze is elevated approximately 60 cm above the floor. Infrared photo-beams that crossed the entrance of each arm and the center of the maze detected the exploratory activity of an animal. Data collection is automated.

The effectiveness of a test compound is determined by the number of entries into open versus enclosed arms and the duration of time spent in each type of arm. Increased entry and time within open arms is interpreted as decreased anxiety and thus an indication of the effectiveness of a test compound as an anxiolytic.

(Pellow S, Chopin P, File S E and Briley M (1985) Validation of open-closed arm entries in an elevated plus-maze as a measure of anxiety in the rat. *J Neurosci Methods* 14:149–167.)

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound of the formula

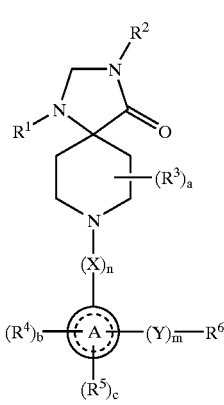

(I)

wherein
  $R^1$ is selected from the group consisting of hydrogen, $C_{1-6}$alkyl, aryl and aralkyl;
  wherein the aryl or aralkyl group is optionally substituted with one to four substituents independently selected from halogen, $C_{1-6}$alkyl, halogenated $C_{1-6}$alkyl, $C_{1-6}$alkoxy, nitro, amino, $(C_{1-6}$alkyl)amino, di$(C_{1-6}$alkyl)amino, $C_{1-6}$alkylsulfonyl, amido, $(C_{1-6}$alkyl)amido, di$(C_{1-6}$alkyl)amido, sulfonyl, aminosulfonyl, $(C_{1-6}$alkyl)aminosulfonyl, di$(C_{1-6}$alkyl)aminosulfonyl or $C_{3-8}$cycloalky;
  $R^2$ is selected from the group consisting of hydrogen, $C_{1-6}$alkyl, $C_{2-6}$alkenyl, $C_{2-6}$alkynyl, hydroxyamino$C_{1-6}$alkyl, aminocarbonyl$C_{1-6}$alkyl, $C_{1-6}$alkoxycarbonyl $C_{1-6}$alkyl, aryl, $C_{3-8}$cycloalkyl, partially unsaturated carbocyclyl, $C_{1-6}$aralkyl, and carbocyclyl$C_{1-6}$alkyl;
  wherein the alkyl group is optionally substituted with one to two substituents independently selected from hydroxy, carboxy, cyano, amino, $C_{1-6}$alkylamino, di$(C_{1-6}$alkyl)amino, hydroxy$C_{1-6}$alkylamino, amino $C_{1-6}$alkylamino, $C_{1-6}$alkylamino$C_{1-6}$alkylamino or di$(C_{1-6}$alkyl)amino$C_{1-6}$alkylamino, wherein the aryl, cycloalkyl, or carbocyclyl, group is optionally substituted with one to four substituents independently selected from halogen, $C_{1-6}$alkyl, halogenated $C_{1-6}$alkyl, $C_{1-6}$alkoxy, nitro, amino, $(C_{1-6}$alkyl)amino, di$(C_{1-6}$alkyl)amino, $C_{1-6}$alkylsulfonyl, amido, $(C_{1-6}$alkyl)amido, di$(C_{1-6}$alkyl)amido, sulfonyl, aminosulfonyl, $(C_{1-6}$alkyl)aminosulfonyl, di$(C_{1-6}$alkyl)aminosulfonyl or $C_{1-4}$alkoxycarbonyl;

a is an integer from 0 to 2;

$R^3$ is selected from the group consisting of $C_{1-4}$alkyl and hydroxy $C_{1-4}$alkyl;

n is an integer from 0 to 1;

X is selected from the group consisting of $C_{1-6}$alkyl, $C_{2-6}$alkenyl, $C_{2-4}$alkyl-O and $C_{2-4}$alkyl-S;

wherein the alkyl group is optionally substituted with one to two substituents independently selected from fluoro, $C_{1-6}$alkyl, fluorinated $C_{1-6}$alkyl, $C_{1-6}$alkoxy, nitro, amino, $(C_{1-6}$alkyl)amino, di$(C_{1-6}$alkyl)amino, $C_{1-6}$alkylsulfonyl, amido, $(C_{1-6}$alkyl)amido, di$(C_{1-6}$alkyl)amido, sulfonyl, aminosulfonyl, $(C_{1-6}$alkyl)aminosulfonyl or di$(C_{1-6}$alkyl)aminosulfonyl;

and wherein X is $C_{2-4}$alkyl-O or $C_{2-4}$alkyl-S, the X group is incorporated into the molecule such that the $C_{2-4}$alkyl is bound directly to the piperidine portion of the molecule;

is phenyl;

b is an integer from 0 to 1;

$R^4$ is selected from the group consisting of aryl, $C_{3-8}$cycloalkyl, and partially unsaturated carbocyclyl;

c is an integer from 0 to 3;

$R^5$ is selected from the group consisting of halogen, $C_{1-6}$alkyl, halogenated $C_{1-6}$alkyl, $C_{1-6}$alkoxy, nitro, amino, $(C_{1-6}$alkyl)amino, di$(C_{1-6}$alkyl)amino, $C_{1-6}$alkylsulfonyl, amido, $(C_{1-6}$alkyl)amido, di$(C_{1-6}$alkyl)amido, sulfonyl, aminosulfonyl, $(C_{1-6}$alkyl)aminosulfonyl or di$(C_{1-6}$alkyl)aminosulfonyl;

m is 0;

Y is selected from the group consisting of $C_{1-4}$alkyl, $C_{2-4}$alkenyl, O, S, NH, N($C_{1-4}$alkyl), $C_{1-6}$alkyl-O, $C_{1-6}$alkyl-S, O—$C_{1-6}$alkyl and S—$C_{1-6}$alkyl-S;

$R^6$ is a heteroaryl selected from the group consisting of furyl, thienyl, pyridyl and imidazolyl;

wherein the heteroaryl group is optionally substituted with one to four substituents independently selected from halogen, hydroxy, $C_{1-6}$alkyl, halogenated $C_{1-6}$alkyl, $C_{1-6}$alkoxy, nitro, amino, $(C_{1-6}$alkyl)amino, di$(C_{1-6}$alkyl)amino, $C_{1-6}$alkylsulfonyl, amido, $(C_{1-6}$alkyl)amido, di$(C_{1-6}$alkyl)amido, sulfonyl, aminosulfonyl, $(C_{1-6}$alkyl)aminosulfonyl, di$(C_{1-6}$alkyl)aminosulfonyl or triphenylmethyl;

and pharmaceutically acceptable salts thereof.

2. A compound as in claim 1 wherein
  $R^1$ is selected from the group consisting of $C_{1-4}$alkyl, aryl and aralkyl;
  wherein the aryl or aralkyl group is optionally substituted with one to three substituents independently selected from halogen, $C_{1-4}$alkyl, fluorinated$C_{1-4}$alkyl, $C_{1-4}$alkoxy, amino, $(C_{1-4}$alkyl)amino, di$(C_{1-4}$alkyl)

amino, amido, (C$_{1-4}$alkyl)amido, di(C$_{1-4}$alkyl)amido or C$_{5-7}$cycloalkyl;

R$^2$ is selected from the group consisting of hydrogen, C$_{1-4}$alkyl, hydroxyaminoC$_{1-4}$alkyl, aminocarbonylC$_{1-4}$alkyl, C$_{1-4}$alkoxycarbonylC$_{1-4}$alkyl, aryl, C$_{5-7}$cycloalkyl, and C$_{1-4}$aralkyl;

wherein the alkyl group is optionally substituted with one to two substituents independently selected from hydroxy, carboxy, cyano, amino, C$_{1-4}$alkylamino, di(C$_{1-4}$alkyl)amino, hydroxyC$_{1-4}$alkylamino, amino C$_{1-4}$alkylamino, C$_{1-4}$alkylaminoC$_{1-4}$alkylamino or di(C$_{1-4}$alkyl)aminoC$_{1-6}$alkylamino, wherein the aryl, or cycloalkyl, group is optionally substituted with one to two substituents independently selected from halogen, C$_{1-4}$alkyl, fluorinatedC$_{1-4}$alkyl, C$_{1-4}$alkoxy, amino, (C$_{1-4}$alkyl)amino, di(C$_{1-4}$alkyl)amino, amido, (C$_{1-4}$alkyl)amido, di(C$_{1-4}$alkyl)amido or C$_{1-4}$alkoxycarbonyl;

a is an integer from 0 to 1;

R$^3$ is selected from the group consisting of C$_{1-4}$alkyl and hydroxyC$_{1-4}$alkyl;

n is an integer from 0 to 1;

X is selected from the group consisting of C$_{1-6}$alkyl, C$_{2-4}$alkyl-O and C$_{2-4}$alkyl-S;

wherein the alkyl group is optionally substituted with one to two substituents independently selected from fluoro, C$_{1-4}$alkyl, fluorinatedC$_{1-4}$alkyl, C$_{1-4}$alkoxy, amino, (C$_{1-4}$alkyl)amino or di(C$_{1-4}$alkyl)amino;

and wherein X is C$_{2-4}$alkyl-O or C$_{2-4}$alkyl-S, the X group is incorporated into the molecule such that the C$_{2-4}$alkyl is bound directly to the piperidine portion of the molecule;

is phenyl;

b is an integer from 0 to 1;

R$^4$ is selected from the group consisting of aryl, and C$_{5-7}$cycloalkyl;

c is an integer from 0 to 2;

R$^5$ is selected from the group consisting of halogen, C$_{1-4}$alkyl, fluorinated C$_{1-4}$alkyl, C$_{1-4}$alkoxy, nitro, amino, (C$_{1-4}$alkyl)amino, di(C$_{1-4}$alkyl)amino, C$_{1-4}$alkylsulfonyl, amido, (C$_{1-4}$alkyl)amido, di(C$_{1-4}$alkyl)amido, sulfonyl, aminosulfonyl, (C$_{1-4}$alkyl)aminosulfonyl or di(C$_{1-4}$alkyl)aminosulfonyl;

m is 0;

Y is selected from the group consisting of C$_{1-4}$alkyl, C$_{2-4}$alkenyl, O, S, NH, N(C$_{1-4}$alkyl), C$_{1-6}$alkyl-O, C$_{1-6}$alkyl-S, O—C$_{1-6}$alkyl and S—C$_{1-6}$alkyl-S;

R$^6$ is a heteroaryl selected from the group consisting of furyl, thienyl, pyridyl and imidazolyl;

wherein the heteroaryl group is optionally substituted with one to two substituents independently selected from halogen, hydroxy, C$_{1-4}$alkyl, fluorinatedC$_{1-4}$alkyl, C$_{1-4}$alkoxy, nitro, amino, (C$_{1-4}$alkyl)amino, di(C$_{1-4}$alkyl)amino, C$_{1-4}$alkylsulfonyl, amido, (C$_{1-4}$alkyl)amido, di(C$_{1-4}$alkyl)amido, sulfonyl, aminosulfonyl, (C$_{1-4}$alkyl)aminosulfonyl, di(C$_{1-4}$alkyl)aminosulfonyl or triphenylmethyl;

and pharmaceutically acceptable salts thereof.

3. A compound as in claim 2 wherein

R$^1$ is selected from the group consisting of C$_{1-4}$alkyl, aryl and aralkyl; wherein the aryl group is optionally substituted with one to three substituent independently selected from halogen, C$_{1-4}$alkyl, C$_{1-4}$alkoxy, trifluoromethyl and C$_{5-6}$cycloalkyl;

R$^2$ is selected from the group consisting of hydrogen, C$_{1-4}$alkyl, hydroxyC$_{1-4}$alkyl, cyanoC$_{1-4}$alkyl, amino C$_{1-4}$alkyl, C$_{1-4}$alkylaminoC$_{1-4}$alkyl, di(C$_{1-4}$alkyl)aminoC$_{1-4}$alkyl, aminocarbonylC$_{1-4}$alkyl, carboxyC$_{1-4}$alkyl, and C$_{1-4}$alkoxycarbonylC$_{1-4}$alkyl;

a is an integer from 0 to 1;

R$^3$ is selected from the group consisting of C$_{1-4}$alkyl;

n is 1;

X is selected from the group consisting of C$_{1-4}$alkyl and C$_{2-4}$alkyl-O;

wherein X is C$_{2-4}$alkyl-O, the X group is incorporated into the molecule such that the C$_{2-4}$alkyl portion is bound directly to the piperidine portion of the molecule;

is selected from the group consisting of phenyl;

b is 0;

c is an integer from 0 to 2;

R$^5$ is selected from the group consisting of halogen, fluorinatedC$_{1-4}$alkyl and C$_{1-4}$alkyl;

m is 0;

Y is selected from the group consisting of O, C$_{1-4}$alkyl-O, C$_{2-4}$alkenyl and C$_{1-4}$alkyl;

R$^6$ is a heteroaryl selected from the group consisting of furyl, thienyl, pyridyl and imidazolyl;

wherein the heteroaryl is optionally substituted with one to two substituents independently selected from halogen, acetyl, hydroxy, C$_{1-4}$alkyl, C$_{1-4}$alkoxy, trifluoromethyl, amino, C$_{1-4}$alkylamino, di(C$_{1-4}$alkyl)amino, cyano, nitro, oxo, t-butoxycarbonyl or triphenylmethyl;

and pharmaceutically acceptable salts thereof.

4. A compound as in claim 3 wherein

R$^1$ is selected from the group consisting of n-propyl, phenyl, 4-fluorophenyl, 3-bromophenyl, 3-chlorophenyl, 3-trifluoromethylphenyl, 4-methylphenyl, 4-methoxyphenyl, 4-cyclopentylphenyl, 4-chloro-3-methylphenyl, 4-fluoro-3,5-dimethylphenyl and benzyl;

R$^2$ is selected from the group consisting of hydrogen, methyl, cyanomethyl, 2-hydroxyethyl, aminoethyl, dimethylaminoethyl, diethylaminoethyl, aminocarbonylmethyl, carboxymethyl, and methoxycarbonylmethyl;

a is an integer from 0 to 1;

R$^3$ is methyl;

n is 1;

X is selected from the group consisting of CH$_2$, and CH$_2$CH$_2$, CH$_2$CH$_2$CH$_2$, CH$_2$CH$_2$CH$_2$CH$_2$ and CH$_2$CH$_2$—O;

is phenyl;

b is 0;

c is an integer from 0 to 2;

$R^5$ is selected from the group consisting of fluoro, chloro, trifluoromethyl and methyl;

m is 0;

$R^6$ is selected from the group consisting of 3-pyridyl, 2-furyl, 3-furyl, 2-thienyl, 3-thienyl, 5-cyano-2-thienyl, 4-methyl-2-thienyl, 3-pyridyl, 1-imidazolyl, 3-imidazolyl, and 1-triphenylmethyl-3-imidazolyl;

and pharmaceutically acceptable salts thereof.

5. A compound as in claim 4 wherein $R^1$ is selected from the group consisting of phenyl, 4-fluorophenyl, 3-trifluoromethylphenyl, 4-methylphenyl, 3-bromophenyl, 3-chlorophenyl, 4-chloro-3-methylphenyl and 4-fluoro-3,5-dimethylphenyl;

$R^2$ is selected from the group consisting of hydrogen, methyl, cyanomethyl, 2-hydroxyethyl, aminoethyl, dimethylaminoethyl, diethylaminoethyl, aminocarbonylmethyl, carboxymethyl, and methoxycarbonylmethyl;

X is selected from the group consisting of $CH_2$, and $CH_2CH_2$, $CH_2$ $CH_2CH_2$ and $CH_2CH_2CH_2CH_2$;

c is an integer from 0 to 1;

$R^5$ is selected from the group consisting of fluoro, trimethylphenyl and methyl;

is phenyl;

$R^6$ is selected from the group consisting of 3-pyridyl, 2-furyl, 3-furyl, 2-thienyl, 3-thienyl, 5-chloro-2-thienyl, 5-methyl-2-thienyl, and 4-methyl-2-thienyl;

and pharmaceutically acceptable salts thereof.

6. A compound as in claim 5 wherein $R^1$ is selected from the group consisting of phenyl, 4-fluorophenyl, 3-trifluoromethylphenyl, 4-methylphenyl, 3-bromophenyl and 4-chloro-3-methylphenyl;

X is selected from the group consisting of $CH_2$, and $CH_2CH_2$ and $CH_2CH_2CH_2$;

is phenyl;

$R^5$ is fluoro;

m is an integer from 0 to 1;

Y is O;

$R^6$ is selected from the group consisting of phenyl, 3-pyridyl, 2-furyl, 3-furyl, 2-thienyl, 3-thienyl, and 4-methyl-2-thienyl;

and pharmaceutically acceptable salts thereof.

7. A compound as in claim 6 wherein $R^1$ is selected from the group consisting of phenyl and 4-fluorophenyl;

$R^2$ is selected from the group consisting of hydrogen, methyl, cyanomethyl, 2-hydroxyethyl, dimethylaminoethyl, aminocarbonylmethyl and methoxycarbonylethyl;

is phenyl $R^6$ is selected from the group consisting of 2-furyl, 2-thienyl and 3-thienyl;

and pharmaceutically acceptable salts thereof.

8. A compound as in claim 1 wherein $R^1$ is selected from the group consisting of hydrogen, $C_{1-6}$alkyl and aryl;

wherein the aryl group is optionally substituted with one to four substituents independently selected from halogen, $C_{1-6}$alkyl, halogenated $C_{1-6}$alkyl, $C_{1-6}$alkoxy, nitro, amino, $(C_{1-6}$alkyl)amino, di$(C_{1-6}$alkyl)amino, $C_{1-6}$alkylsulfonyl, amido, $(C_{1-6}$alkyl)amido, di$(C_{1-6}$alkyl)amido, sulfanyl, aminosulfonyl, $(C_{1-6}$alkyl)aminosulfonyl, di$(C_{1-6}$alkyl)aminosulfonyl or $C_{3-8}$cycloalky;

$R^2$ is selected from the group consisting of hydrogen, $C_{1-6}$alkyl, $C_{2-6}$alkenyl, $C_{2-6}$alkynyl, hydroxyamino$C_{1-6}$alkyl, aminocarbonyl$C_{1-6}$alkyl, $C_{1-6}$alkoxycarbonyl $C_{1-6}$alkyl, aryl, $C_{3-8}$cycloalkyl, partially unsaturated carbocyclyl, $C_{1-6}$aralkyl, and carbocyclyl$C_{1-6}$alkyl;

wherein the alkyl group is optionally substituted with one to two substituents independently selected from hydroxy, carboxy, cyano, amino, $C_{1-6}$alkylamino, di$(C_{1-6}$alkyl)amino, hydroxy$C_{1-6}$alkylamino, amino $C_{1-6}$alkylamino, $C_{1-6}$alkylamino$C_{1-6}$alkylamino or di$(C_{1-6}$alkyl)amino$C_{1-6}$alkylamino, wherein the aryl, cycloalkyl, or carbocyclyl, group is optionally substituted with one to four substituents independently selected from halogen, $C_{1-6}$alkyl, halogenated $C_{1-6}$alkyl, $C_{1-6}$alkoxy, nitro, amino, $(C_{1-6}$alkyl)amino, di$(C_{1-6}$alkyl)amino, $C_{1-6}$alkylsulfonyl, amido, $(C_{1-6}$alkyl)amido, di$(C_{1-6}$alkyl)amido, sulfonyl, aminosulfonyl, $(C_{1-6}$alkyl)aminosulfonyl or di$(C_{1-6}$alkyl)aminosulfonyl;

a is an integer from 0 to 2;

$R^3$ is selected from the group consisting of $C_{1-4}$alkyl and hydroxy $C_{1-4}$alkyl;

n is an integer from 0 to 1;

X is selected from the group consisting of $C_{1-6}$alkyl, $C_{2-6}$alkenyl, $C_{2-4}$alkyl-O and $C_{2-4}$alkyl-S;

wherein the alkyl group is optionally substituted with one to two substituents independently selected from fluoro, $C_{1-6}$alkyl, fluorinated $C_{1-6}$alkyl, $C_{1-6}$alkoxy, nitro, amino, $(C_{1-6}$alkyl)amino, di$(C_{1-6}$alkyl)amino, $C_{1-6}$alkylsulfonyl, amido, $(C_{1-6}$alkyl)amido, di$(C_{1-6}$alkyl)amido, sulfonyl, aminosulfonyl, $(C_{1-6}$alkyl)aminosulfonyl or di$(C_{1-6}$alkyl)aminosulfonyl;

and wherein X is $C_{2-4}$alkyl-O or $C_{2-4}$alkyl-S, the X group is incorporated into the molecule such that the $C_{2-4}$alkyl is bound directly to the piperidine portion of the molecule;

is phenyl;

b is an integer from 0 to 1;

$R^4$ is selected from the group consisting of aryl, $C_{3-8}$cycloalkyl, and partially unsaturated carbocyclyl;

c is an integer from 0 to 3;

$R^5$ is selected from the group consisting of halogen, $C_{1-6}$alkyl, halogenated $C_{1-6}$alkyl, $C_{1-6}$alkoxy, nitro, amino, $(C_{1-6}$alkyl)amino, di$(C_{1-6}$alkyl)amino, $C_{1-6}$alkylsulfonyl, amido, $(C_{1-6}$alkyl)amido, di$(C_{1-6}$alkyl)amido, sulfonyl, aminosulfonyl, $(C_{1-6}$alkyl)aminosulfonyl or di$(C_{1-6}$alkyl)aminosulfonyl;

m is an integer from 0;

$R^6$ is heteroaryl, furyl, thienyl, pyridyl and imidazolyl;

wherein the heteroaryl group is optionally substituted with one to four substituents independently selected from halogen, hydroxy, $C_{1-6}$alkyl, halogonated $C_{1-6}$alkyl, $C_{1-6}$alkoxy, nitro, amino, $(C_{1-6}$alkyl)amino, di$(C_{1-6}$alkyl)amino, $C_{1-6}$alkylsulfonyl, amido, $(C_{1-6}$alkyl)amido, di$(C_{1-6}$alkyl)amido, sulfonyl, aminosulfonyl, $(C_{1-6}$alkyl)aminosulfonyl or di$(C_{1-6}$alkyl)aminosulfonyl;

and pharmaceutically acceptable salts thereof.

9. A pharmaceutical composition comprising a pharmaceutically acceptable carrier and a compound of claim 1.

10. A process for making a pharmaceutical composition comprising mixing a compound of claim 1 and a pharmaceutically acceptable carrier.

11. A method of treating a disorder mediated by the ORL-1 receptor, wherein the disorder mediated by the ORL-1 receptor is selected from the group consisting of anxiety, depression, substance abuse, neuropathic pain, acute pain, migraine, asthma, cough and improved cognition in a subject in need thereof comprising administering to the subject a therapeutically effective amount of the compound of claim 1.

12. A method of treating a disorder mediated by the ORL-1 receptor, wherein the disorder mediated by the ORL-1 receptor is selected from the group consisting of anxiety, depression, substance abuse, neuropathic pain, acute pain, migraine, asthma, cough and improved cognition in a subject in need thereof comprising administering to the subject a therapeutically effective amount of the composition of claim 9.

13. A method of treating a condition selected from the group consisting of anxiety, depression, substance abuse, neuropathic pain, acute pain, migraine, asthma, cough and improved cognition, in a subject in need thereof comprising administering to the subject a therapeutically effective amount of the compound of claim 1.

14. A method of treating a condition selected from the group consisting of anxiety, depression, substance abuse, neuropathic pain, acute pain, migraine, asthma, cough and improved cognition, in a subject in need thereof comprising administering to the subject a therapeutically effective amount of the composition of claim 9.

* * * * *